(12) United States Patent
Trakht

(10) Patent No.: US 6,197,582 B1
(45) Date of Patent: Mar. 6, 2001

(54) DEVELOPMENT OF HUMAN MONOCLONAL ANTIBODIES AND USES THEREOF

(75) Inventor: Ilya Trakht, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 09/040,833

(22) Filed: Mar. 18, 1998

(51) Int. Cl.[7] .............................. C12N 5/06; C12N 5/16; C12N 5/00; C12N 5/12; G01N 33/567

(52) U.S. Cl. ..................... 435/326; 435/7.21; 435/330; 435/332; 435/333; 435/339; 435/346; 435/372

(58) Field of Search .................................... 435/326, 7.21, 435/330, 332, 333, 339, 346, 372

(56) References Cited

U.S. PATENT DOCUMENTS 4,714,681 * 12/1987 Reading .

* cited by examiner

*Primary Examiner*—Lynette R. F. Smith
*Assistant Examiner*—Li Lee
(74) *Attorney, Agent, or Firm*—John P. White; Cooper & Dunham LLP

(57) ABSTRACT

The present invention provides a trioma cell which does not produce any antibody obtained by fusing a hetermomyeloma cell which does not produce any antibody with a human lymphoid cell, wherein the heteromyeloma cell is designated B6B11. The invention also provides a tetroma cell capable of producing a monoclonal antibody having specific binding affinity for an antigen obtained by fusing a trioma cell which does not produce any antibody with a human lymphoid cell capable of producing antibody having specific binding affinity for the antigen. The invention also provides methods for generating trioma cells and tetroma cells, and the cells generated by the methods.

9 Claims, 7 Drawing Sheets

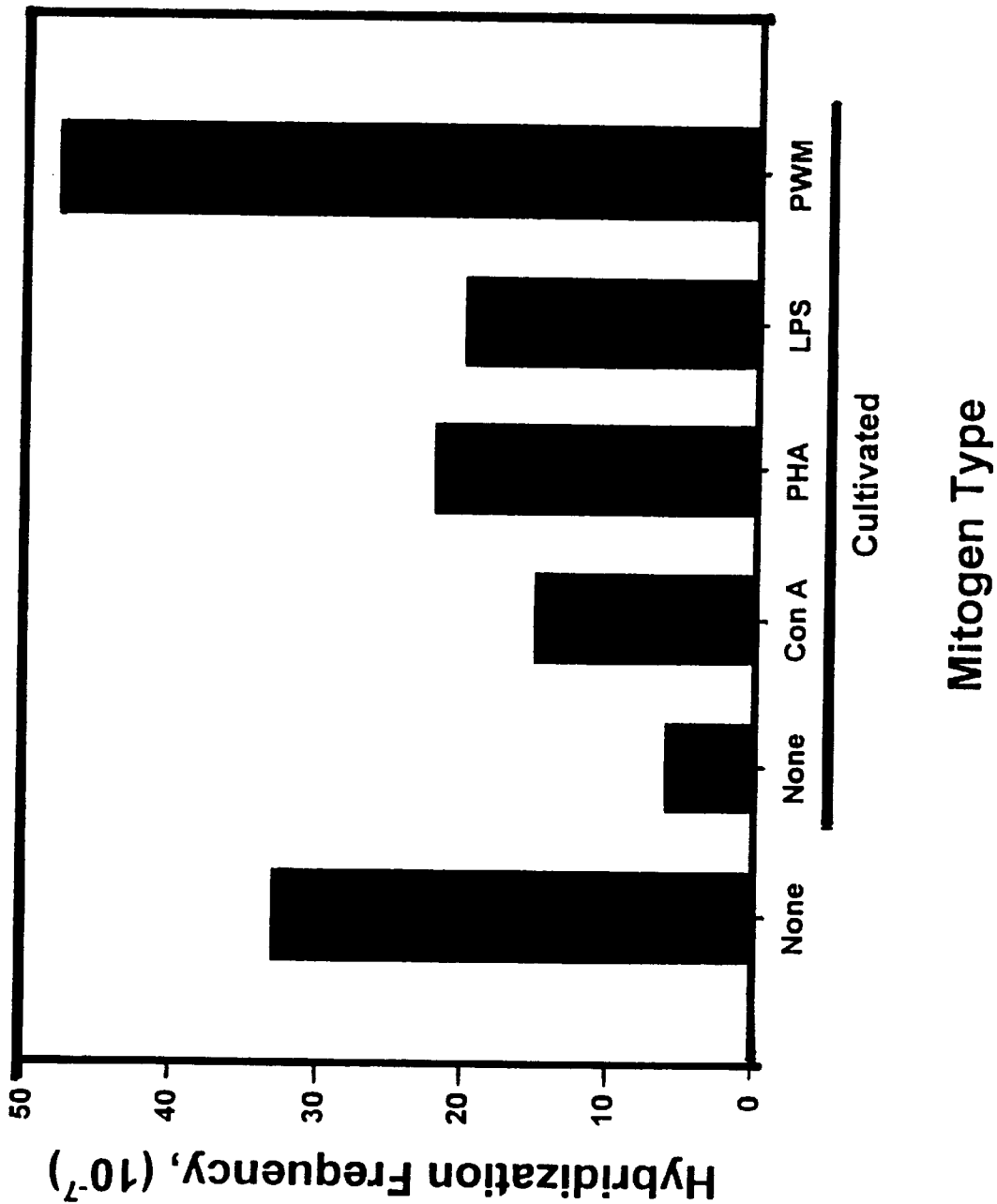

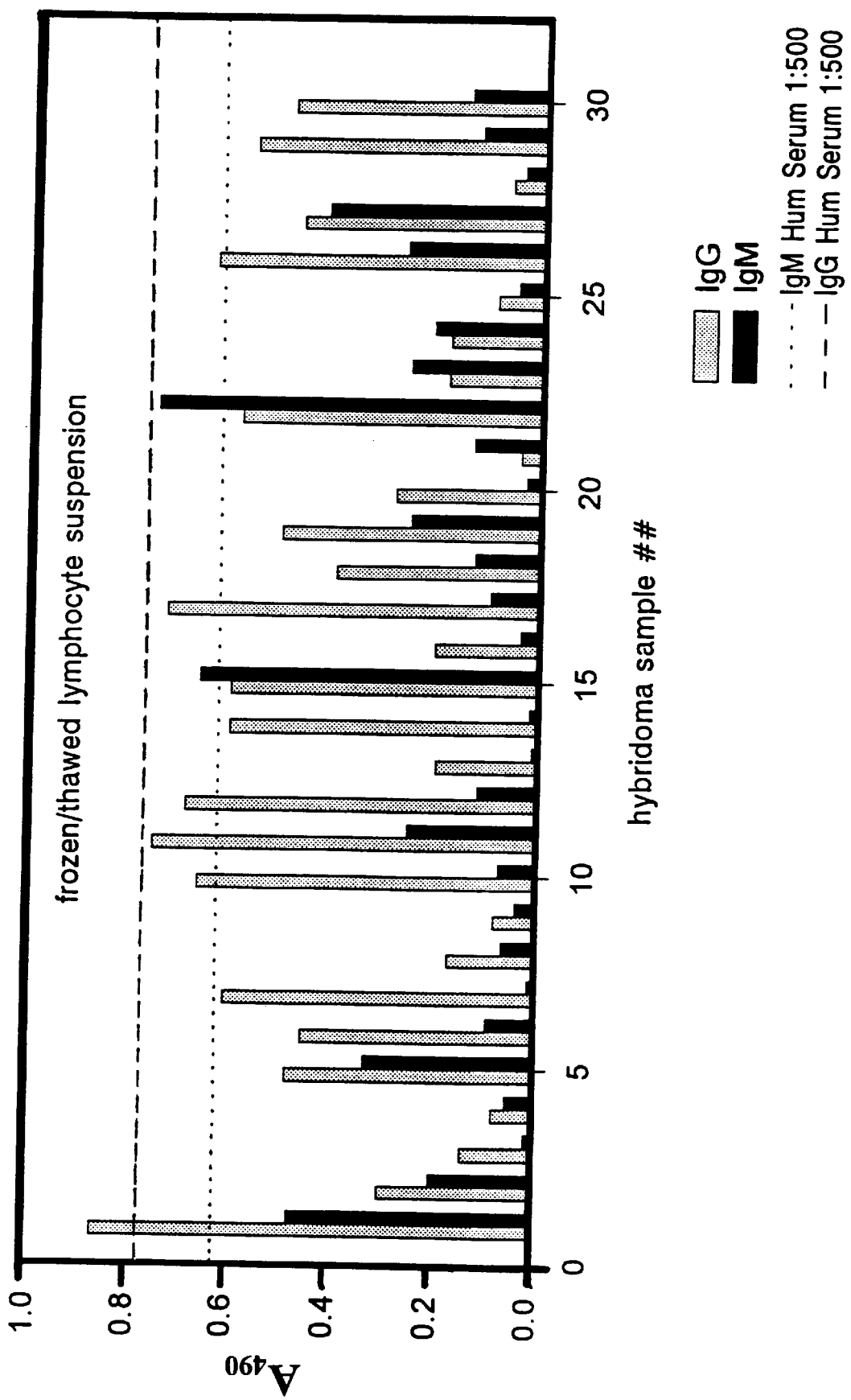

DEVELOPMENT OF HUMAN MONOCLONAL ANTIBODIES AND USES THEREOF

Throughout this application, various publications are referenced by author and date. Full citations for these publications may be found listed alphabetically at the end of the specification immediately preceding the claims. The disclosures of these publications in their entireties are hereby incorporated by reference into this application in order to more fully describe the state of the art.

BACKGROUND OF THE INVENTION

The seminal discovery by Kohler and Milstein (Kohler, G. and Milstein, C., 1975) of mouse "hybridomas" capable of secreting specific monoclonal antibodies (mAbs) against predefined antigens ushered in a new era in experimental immunology. Many problems associated with antisera were circumvented. Clonal selection and immortality of hybridoma cell lines assured monoclonality and permanent availability of antibody products. At the clinical level, however, the use of such antibodies is clearly limited by the fact that they are foreign proteins and act as antigens to humans.

Since the report of Kohler and Milstein (Kohler, G. and Milstein, C., 1975), the production of mouse monoclonal antibodies has become routine. However, the application of xenogenic mAbs for in vivo diagnostics and therapy is often associated with undesirable effects such as a human anti-mouse immunoglobulin response. mAbs have great potential as tools for imaging; therapeutic treatment has motivated the search into the means of production of human mAbs (humAbs) (Levy, R., and Miller R A., 1983). However, progress in this area has been hampered by the absence of human myelomas suitable as fusion partners with the characteristics similar to those of mouse myeloma cells (Posner M R, et al., 1983). The use of Epstein-Barr virus (EBV) has proved to be quite efficient for human lymphocyte immortalization (Kozbor D, and Roder J., 1981; Casual O, 1986), but has certain limitations such as low antibody secretion rate, poor clonogenicity of antibody-secreting lines and chromosomal instability requiring frequent subcloning. Undifferentiated human lymphoblastoid cell lines appear more attractive. In contrast to differentiated myeloma cells, these cell lines are readily adapted to culture conditions, though the problems of low yield and unstable secretion remain unresolved (Glassy M C, 1983; Ollson L, et al., 1983). The best potential fusion partners are syngenic myeloma cells with well-developed protein synthesis machinery (Nilsson K. and Ponten J., 1975). However, culturing difficulties explain why few lines have been conditioned for in vitro growth and capability to produce viable hybrids (Goldman-Leikin R E, 1989). Existing myelomas have low fusion yield and slow hybrid growth, although mAb production is relatively stable (Brodin T, 1983). Genetic instability is a major disadvantage of interspecies hybrids. This is the case, for example, when a mouse myeloma is used as the immortalizing partner. Production of mouse-human cell hybrids is not difficult. In vitro these cells have growth characteristics similar to those of conventional mouse-mouse hybridomas (Teng N N H, 1983). However, spontaneous elimination of human chromosomes considerably reduces the probability of stable mAb secretion (Weiss M C, and Green H., 1967). In order to improve growth characteristics and stability of humAb production, hetero-hybrids between mouse myeloma cells and human lymphocyte (Oestberg L, and Pursch E., 1983) as well as heteromyelomas (Kozbor D, et. al., 1984) are used as the fusion partners.

SUMMARY OF THE INVENTION

The present invention provides a heteromyeloma cell which does not produce any antibody, capable of producing a trioma cell which does not produce any antibody, when fused with a human lymphoid cell, wherein the trioma cell is capable of producing a tetroma cell capable of producing a monoclonal antibody having specific binding affinity for an antigen, when fused with a second human lymphoid cell, the second human lymphoid cell being capable of producing antibody having specific binding affinity for the antigen, with the proviso that the heteromyeloma cell is not B6B11 (ATCC Designation Number HB-12481).

The present invention further provides a trioma cell obtained by fusing a heteromyeloma cell which does not produce any antibody with a human lymphoid cell.

The present invention also provides a tetroma cell capable of producing a monoclonal antibody having specific binding affinity for an antigen, obtained by fusing the described trioma cell which does not produce any antibody with a human lymphoid cell capable of producing antibody having specific binding affinity for the antigen.

The present invention additionally provides a monoclonal antibody produced by the described tetroma.

The present invention further provides a method of generating the described trioma cell comprising: (a) fusing a heteromyeloma cell which does not produce any antibody with a human lymphoid cell thereby forming a trioma cell; (b) incubating the trioma cell formed in step (a) under conditions permissive to the production of antibody by the trioma cell; and (c) selecting a trioma fusion cell that does not produce any antibody.

Still further, the present invention provides a method of generating a tetroma cell comprising: (a) fusing the described trioma cell with a human lymphoid cell, thereby forming a tetroma cell; (b) incubating the tetroma cell formed in step (a) under conditions permissive to the production of antibody by the tetroma cell; and (c) selecting a tetroma cell capable of producing a monoclonal antibody.

The present invention also provides a method of producing a monoclonal antibody comprising (a) fusing a lymphoid cell capable of producing of producing antibody with the described trioma cell, thereby forming a tetroma cell; and (b) incubating the tetroma cell formed in step (a) under conditions permissive to the production of antibody by the tetroma cell, thereby producing the monoclonal antibody.

Also the present invention provides a method of producing a monoclonal antibody specific for an antigen associated with a condition in a subject comprising: (a) fusing a lymphoid cell capable of producing antibody with the described trioma cell, thereby forming a tetroma cell; (b) incubating the tetroma cell formed in step (a) under conditions permissive to the production of antibody by the tetroma cell; (c) selecting a tetroma cell producing a monoclonal antibody; (d) contacting the monoclonal antibody of step (c) with (1) a sample from a subject with the condition or (2) a sample from a subject without the condition under conditions permissive to the formation of a complex between the monoclonal antibody and the sample; (e) detecting the complex formed between the monoclonal antibody and the sample; (f) determining the amount of complex formed in step (e); and (g) comparing the amount of complex determined in step (f) for the sample from the subject with the condition with amount determined in step (f) for the sample from the subject without the condition, a greater amount of complex formation for the sample from the subject with the condition indicating that a monoclonal antibody specific for the antigen specific for the condition is produced.

Additionally, the present invention provides a method of identifying an antigen associated with a condition in a sample comprising: (a) contacting the monoclonal antibody produced by the described method with the sample under conditions permissive to the formation of a complex between the monoclonal antibody and the sample; (b) detecting the complex formed in step (a); and (c) isolating the complex detected in step (b), thereby identifying the antigen associated with the condition in the sample.

The present invention additionally provides a method of diagnosing a condition in a subject comprising: (a) contacting a sample from the subject with a monoclonal antibody produced by the described method under conditions permissive to the formation of a complex between the monoclonal antibody and the sample; and (b) detecting the formation of a complex between the monoclonal antibody and the sample, positive detection indicating the presence of an antigen specific for the condition in the sample, thereby diagnosing the condition in the subject.

The present invention further provides a composition comprising the produced monoclonal antibody and a suitable carrier.

Further, the present invention also provides a therapeutic composition comprising an effective amount of the produced monoclonal antibody and a pharmaceutically acceptable carrier.

Also, the present invention further provides a method of treating a condition in a subject comprising administering to the subject an amount of the described therapeutic composition effective to bind the antigen associated with the condition, thereby treating the condition in the subject.

Finally, the present invention provides a method of preventing a condition in a subject comprising administering to the subject an amount of the described therapeutic composition, effective to bind the antigen associated with the condition, thereby preventing the condition in the subject.

BRIEF DESCRIPTION OF THE FIGURES

FIG. 3 B6B11 fusion efficiency with fresh isolated and cultured splenocytes. SPL were isolated in LSM, immediately after a portion of the cells were fused with B6B11 cells and the remaining SPL were cultivated in vitro for 7–9 days in RPMI-C containing 15% FCS in the presence of ConA, LPS, PHA, PWM or without mitogens, then these cells were also fused with B6B11. PWM in the concentration of 5 μg/ml influenced effectively the fusion efficiency.

FIGS. 5A–5B Immunoglobulin production by hybridomas (tetromas) derived from the fusion of PBLs with MFP-2. FIG. 5A shows results of fusing fresh lymphocyte suspensions with MFP-2. FIG. 5B shows results of fusing frozen/thawed lymphocyte suspensions with MFP-2. The dark rectangles indicate IgM production. The gray rectangles indicate IgG production. The Y-axis indicates optical density at $A_{490}$ for different hybridoma samples (tetromas) generated from fusion with the MFP-2 trioma line (X-axis). The dotted line indicates the optical density at $A_{490}$ for a 1:500 dilution of IgM antibody. The dashed line indicates the optical density at $A_{490}$ for a 1:500 dilution of IgG antibody.

DETAILED DESCRIPTION OF THE INVENTION

Figure 1A:
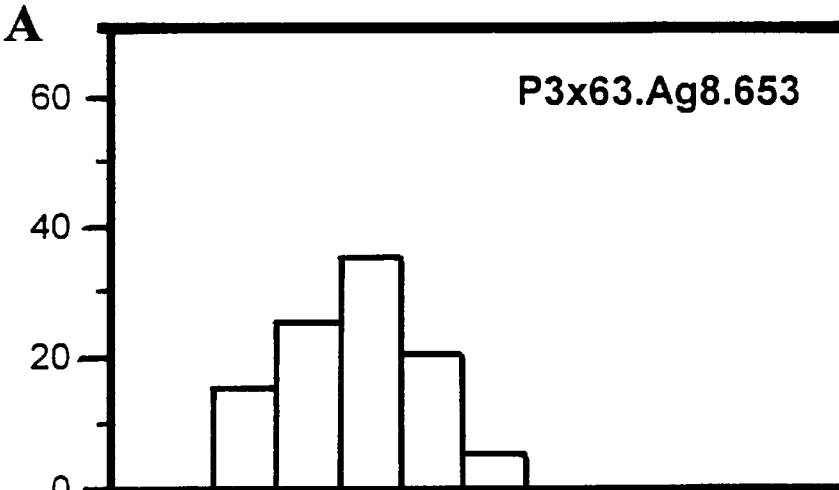
FIGS. 1A–1C Distribution of cells according to the number of chromosomes. The X-axis indicates the amount of chromosomes. The Y-axis indicates the percentage of cells with appropriate number of chromosomes. The data represent the average ones based on the analysis of more than 50 metaphase plates for each line: P3.X63.Ag8.653 FIG. 1A, RPMI 8226 FIG. 1B, B6B11 FIG. 1C.

The present invention provides a heteromyeloma cell which does not produce any antibody, capable of producing a trioma cell which does not produce any antibody, when fused with a human lymphoid cell, wherein the trioma cell is capable of producing a tetroma cell capable of producing a monoclonal antibody having specific binding affinity for an antigen, when fused with a second human lymphoid cell, the second human lymphoid cell being capable of producing antibody having specific binding affinity for the antigen, with the proviso that the heteromyeloma cell is not B6B11 (ATCC Designation number HB-12481). Heteromyeloma cell B6B11 was deposited on Mar. 17, 1998 with the American Type Culture Collection (ATCC), 10801 University Boulevard, Manassas, Va., U.S.A. under the provisions of the Budapest Treaty for the International Recognition of the Deposit of Microorganism for the Purposes of Patent Procedure. B6B11 was accorded ATCC Designation Number HB-12481.

The present invention provides a trioma cell obtained by fusing a heteromyeloma cell which does not produce any antibody with a human lymphoid cell. In an embodiment of this invention, the heteromyeloma cell is designated B6B11 (ATCC Designation number HB-12481). In another embodiment, the trioma is a B6B11-like cell. In an embodiment of this invention, the human lymphoid cell is a myeloma cell. In another embodiment of this invention, the human lymphoid cell is a splenocyte or a lymph node cell (lymphocyte). According to an embodiment of this invention, the trioma cell is designated MFP-2 (ATCC Designation number HB-12482). Trioma cell MFP-2 was deposited on Mar. 17, 1998 with the American Type Culture Collection (ATCC), 10801 University Boulevard, Manassas, Va., U.S.A. under the provisions of the Budapest Treaty for the International Recognition of the Deposit of Microorganism for the Purposes of Patent Procedure. MFP-2 was accorded ATCC Designation Number HB-12482.

The present invention also provides a tetroma cell capable of producing a monoclonal antibody having specific binding affinity for an antigen, obtained by fusing the described trioma cell which does not produce any antibody with a human lymphoid cell capable of producing antibody having specific binding affinity for the antigen. According to an embodiment of this invention, the human lymphoid cell is a peripheral blood lymphocyte, a splenocyte, a lymph node cell, a B cell, a T cell, a tonsil gland lymphocyte, a monocyte, a macrophage, an erythroblastoid cell or a Peyer's patch cell. In an embodiment of this invention, the trioma cell is designated MFP-2 (ATCC Designation number HB-12482).

According to an embodiment of this invention, the antigen is a tumor-associated antigen, a cell-specific antigen, a tissue-specific antigen, an enzyme, a nucleic acid, an immunoglobulin, a toxin, a viral antigen, a bacterial antigen or a eukaryotic antigen. In one embodiment, the antigen is a mammalian, insect, fungal, $E.$ $coli$ or Klebsiella antigen.

The present invention provides a monoclonal antibody produced by the described tetroma. The present invention also provides an isolated nucleic acid encoding the monoclonal antibody produced by the described tetroma. The nucleic acid may include, but is not limited to DNA, RNA, cDNA, oligonucleotide analogs, vectors, expression vectors or probes. Additionally, the present invention contemplates the expression of the nucleic acid encoding the monoclonal antibody introduced into a host cell capable of expression the monoclonal antibody or portions thereof.

The present invention further provides a method of generating the described trioma cell comprising: (a) fusing a heteromyeloma cell which does not produce any antibody with a human lymphoid cell thereby forming a trioma cell; (b) incubating the trioma cell formed in step (a) under conditions permissive to the production of antibody by the trioma cell; and (c) selecting a trioma fusion cell that does not produce any antibody.

According to one embodiment of this invention, the heteromyeloma cell of step (a) is designated B6B11 (ATCC Designation number HB-12481). According to an embodiment of this invention, the human lymphoid cell is a lymph node lymphocyte or a splenocyte. According to an embodiment of the present invention, the method further comprises selecting a trioma cell capable of growth in serum-free media. Another embodiment further comprises selecting a trioma cell that is capable of fusing with a peripheral blood lymphocyte or lymph node lymphocyte. The present invention provides a trioma cell generated by the described method.

Still further, the present invention provides a method of generating a tetroma cell comprising: (a) fusing the described trioma cell with a human lymphoid cell thereby forming a tetroma cell; (b) incubating the tetroma cell formed in step (a) under conditions permissive to the production of antibody by the tetroma cell; and (c) selecting a tetroma cell capable of producing a monoclonal antibody. According to one embodiment of this invention, the trioma cell of step (a) is designated MFP-2 (ATCC Designation number HB-12482). According to an embodiment of this invention, the human lymphoid cell is a peripheral blood lymphocyte, a splenocyte, a lymph node cell, a B cell, a T cell, a tonsil gland lymphocyte, a monocyte, a macrophage, an erythroblastoid cell or a Peyer's patch cell. In an embodiment of this invention, the human lymphoid cell produces antibodies having specific binding affinity for an antigen and wherein the tetroma cell produces a monoclonal antibody having specific binding affinity for the antigen. According to an embodiment of this invention, the antigen is a tumor-associated antigen, a cell-specific antigen, a tissue-specific antigen, an enzyme, a nucleic acid, an immunoglobulin, a toxin, a viral antigen, a bacterial antigen or a eukaryotic antigen. In an embodiment of this invention, the antigen is a mammalian, insect, $E.$ $coli$ or Klebsiella antigen. The present invention further provides a tetroma cell generated by the described method.

The present invention also provides a method of producing a monoclonal antibody comprising (a) fusing a lymphoid cell capable of producing antibody with the described trioma cell, thereby forming a tetroma cell; and (b) incubating the tetroma cell formed in step (a) under conditions permissive to the production of antibody by the tetroma cell, thereby producing the monoclonal antibody.

Also, the present invention provides a method of producing a monoclonal antibody specific for an antigen associated with a condition in a subject comprising: (a) fusing a lymphoid cell capable of producing antibody with the described trioma cell, thereby forming a tetroma cell; (b) incubating the tetroma cell formed in step (a) under conditions permissive to the production of antibody by the tetroma cell; (c) selecting a tetroma cell producing a monoclonal antibody; (d) contacting the monoclonal antibody of step (c) with (1) a sample from a subject with the condition or (2) a sample from a subject without the condition under conditions permissive to the formation of a complex between the monoclonal antibody and the sample; (e) detecting the complex formed between the monoclonal antibody and the sample; (f) determining the amount of complex formed in step (e); and (g) comparing the amount of complex determined in step (f) for the sample from the subject with the condition with amount determined in step (f) for the sample from the subject without the condition, a greater amount of complex formation for the sample from the subject with the condition indicating that a monoclonal antibody specific for the antigen specific for the condition is produced.

In one embodiment of the present invention, step (a) further comprises freezing the lymphoid cell. According to one embodiment of the present invention, step (c) further comprises incubating the selected tetroma cell under conditions permissive to cell replication. According to an embodiment of this invention, the tetroma replication is effected in vitro or in vivo. According to one embodiment of this invention, the trioma cell is designated MFP-2 (ATCC Designation No. HB-12482). The present invention provides a monoclonal antibody specific for an antigen associated with a condition, identified by the described method. The present invention also provides an isolated nucleic acid encoding the described monoclonal antibody. The nucleic acid may include, but is not limited to DNA, RNA, cDNA, oligonucleotide analogs, vectors, expression vectors or probes. Additionally, the present invention contemplates the expression of the nucleic acid encoding the monoclonal antibody introduced into a host cell capable of expression the monoclonal antibody or portions thereof.

According to an embodiment of this invention, the condition is associated with a cancer, a tumor, a toxin, an infectious agent, an enzyme dysfunction, a hormone dysfunction, an autoimmune disease, an immune dysfunction, a viral antigen, a bacterial antigen, a eukaryotic antigen, rejection of a transplanted tissue, poisoning, or venom intoxication. Additionally the condition may be any other abnormality, including that resulting from infection, cancer, autoimmune dysfunction, cardiovascular disease, or transplantation. In an embodiment of this invention, the condition is septicemia, sepsis, septic shock, viremia, bacteremia or fungemia. In an embodiment of this invention, the cancer is lung cancer, liver cancer, leukemia, lymphoma, neuroblastoma, glioma, meningioma, bone cancer, thyroid cancer, breast cancer or prostate cancer. According to an embodiment of this invention, the infectious agent is Hanta virus, HTLV I, HTLV II, HIV, herpes virus, influenza virus, Ebola virus, human papilloma virus, Staphlococcus, Streptococcus, Klebsiella, *E. coli*, anthrax or cryptococcus. According to an embodiment of this invention, the toxin is tetanus, anthrax, botulinum snake venom or spider venom. In one embodiment of this invention, the tumor is benign. In another embodiment, the enzyme dysfunction is hyperactivity or overproduction of the enzyme. In still another embodiment, the hormone dysfunction is hyperactivity or overproduction of the hormone. In yet another embodiment of this invention, the immune dysfunction is CD3 or CD4 mediated. In still another embodiment of this invention, the autoimmune disease is lupus, thyroidosis, graft versus host disease, transplantation rejection or rheumatoid arthritis. In still another embodiment of the invention, the condition is any abnormality. In still another embodiment, the condition is the normal condition.

Additionally, the present invention provides a method of identifying an antigen associated with a condition in a sample comprising: (a) contacting the monoclonal antibody produced by the described method with the sample under conditions permissive to the formation of a complex between the monoclonal antibody and the sample; (b) detecting the complex formed in step (a); and (c) isolating the complex detected in step (b), thereby identifying the antigen associated with the condition in the sample.

An embodiment of this invention, further comprises separating the monoclonal antibody from the monoclonal antibody-antigen complex. In another embodiment the separation is by size fractionation. According to one embodiment, the size fractionation is effected by polyacrylamide or agarose gel electrophoresis.

According to an embodiment of this invention, the condition is associated with a cancer, a tumor, a toxin, an infectious agent, an enzyme dysfunction, a hormone dysfunction, an autoimmune disease, an immune dysfunction, a viral antigen, a bacterial antigen, a eukaryotic antigen, rejection of a transplanted tissue, poisoning, or venom intoxication. Additionally the condition may be any other abnormality, including that resulting from infection, cancer, autoimmune dysfunction, cardiovascular disease, or transplantation. In an embodiment of this invention, the condition is septicemia, sepsis, septic shock, viremia, bacteremia or fungemia. In an embodiment of this invention, the cancer is lung cancer, liver cancer, leukemia, lymphoma, neuroblastoma, glioma, meningioma, bone cancer, thyroid cancer, breast cancer or prostate cancer. According to an embodiment of this invention, the infectious agent is Hanta virus, HTLV I, HTLV II, HIV, herpes virus, influenza virus, Ebola virus, human papilloma virus, Staphlococcus, Streptococcus, Klebsiella, *E. coli*, anthrax or cryptococcus. According to an embodiment of this invention, the toxin is tetanus, anthrax, botulinum, snake venom or spider venom. In one embodiment of this invention, the tumor is benign. In another embodiment, the enzyme dysfunction is hyperactivity or overproduction of the enzyme. In still another embodiment, the hormone dysfunction is hyperactivity or overproduction of the hormone. In yet another embodiment of this invention, the immune dysfunction is CD3 or CD4 mediated. In still another embodiment of this invention, the autoimmune disease is lupus, thyroidosis, graft versus host disease, transplantation rejection or rheumatoid arthritis. In still another embodiment of the invention, the condition is any abnormality. In still another embodiment, the condition is the normal condition.

The present invention additionally provides a method of diagnosing a condition in a subject comprising: (a) contacting a sample from the subject with a monoclonal antibody produced by the described method under conditions permissive to the formation of a complex between the monoclonal antibody and the sample; and (b) detecting the formation of a complex between the monoclonal antibody and the sample, positive detection indicating the presence of an antigen specific for the condition in the sample, thereby diagnosing the condition in the subject.

According to an embodiment of this invention, the monoclonal antibody is coupled to a detectable marker. In an embodiment of this invention, the detectable marker is a radiolabeled molecule, a fluorescent molecule, an enzyme, a ligand, a colorimetric marker or a magnetic bead.

According to an embodiment of this invention, the condition is associated with a cancer, a tumor, a toxin, an infectious agent, an enzyme dysfunction, a hormone dysfunction, an autoimmune disease, an immune dysfunction, a viral antigen, a bacterial antigen, a eukaryotic antigen, rejection of a transplanted tissue, poisoning, or venom intoxication. Additionally the condition may be any other abnormality, including that resulting from infection, cancer, autoimmune dysfunction, cardiovascular disease, or transplantation. In an embodiment of this invention, the condition is septicemia, sepsis, septic shock, viremia, bacteremia or fungemia. In an embodiment of this invention, the cancer is lung cancer, liver cancer, leukemia, lymphoma, neuroblastoma, glioma, meningioma, bone cancer, thyroid cancer, breast cancer or prostate cancer. According to an embodiment of this invention, the infectious agent is Hanta virus, HTLV I, HTLV II, HIV, herpes virus, influenza virus, Ebola virus, human papilloma virus, Staphlococcus, Streptococcus, Klebsiella, *E. coli*, anthrax or cryptococcus. According to an embodiment of this invention, the toxin is tetanus, anthrax, botulinum, snake venom or spider venom. In one embodiment of this invention, the tumor is benign. In another embodiment, the enzyme dysfunction is hyperactivity or overproduction of the enzyme. In still another embodiment, the hormone dysfunction is hyperactivity or overproduction of the hormone. In yet another embodiment of this invention, the immune dysfunction is CD3 or CD4 mediated. In still another embodiment of this invention, the autoimmune disease is lupus, thyroidosis, graft versus host disease, transplantation rejection or rheumatoid arthritis. In still another embodiment of the invention, the condition is any abnormality. In still another embodiment, the condition is the normal condition.

The present invention further provides a composition comprising the produced monoclonal antibody and a suitable carrier.

Further, the present invention also provides a therapeutic composition comprising an effective amount of the produced monoclonal antibody and a pharmaceutically acceptable carrier.

According to an embodiment of this invention, the condition is cancer and the amount of monoclonal antibody is sufficient to inhibit the growth of or eliminate the cancer. According to an embodiment, the condition is an infection and the amount of monoclonal antibody is sufficient to inhibit the growth of or kill the infectious agent. According to an embodiment of this invention, the condition is associate with a toxin and the amount of monoclonal antibody is sufficient to reduce the amount of or destroy the toxin. In still another embodiment, the condition is an autoimmune disease and the amount of monoclonal antibody is sufficient to reduce the amount of or destroy the offending antibody or subunit(s) thereof. In still another embodiment, the condition is a cardiovascular disease and the amount of monoclonal antibody is sufficient to reduce the condition. In yet another embodiment, the condition is a transplantation rejection, and the amount of monoclonal antibody is sufficient to reduce the condition.

According to an embodiment of this invention, the monoclonal antibody is coupled to an effector compound. In an embodiment of this invention, the effector compound is a cytotoxic agent, drug, enzyme, dye, or radioisotope. In an embodiment of this invention, the monoclonal antibody is coupled to a carrier. According to one embodiment of this invention, the carrier is a liposome.

Also, the present invention further provides a method of treating a condition in a subject comprising administering to the subject an amount of the described therapeutic composition effective to bind the antigen associated with the condition, thereby treating the condition in the subject. According to one embodiment of this invention, the therapeutic composition is administered to a second subject.

According to an embodiment of this invention, the condition is associated with a cancer, a tumor, a toxin, an infectious agent, an enzyme dysfunction, a hormone dysfunction, an autoimmune disease, an immune dysfunction, a viral antigen, a bacterial antigen, a eukaryotic antigen, rejection of a transplanted tissue, poisoning, or venom intoxication. Additionally the condition may be any other abnormality, including that resulting from infection, cancer, autoimmune dysfunction, cardiovascular disease, or transplantation. In an embodiment of this invention, the condition is septicemia, sepsis, septic shock, viremia, bacteremia or fungemia. In an embodiment of this invention, the cancer is lung cancer, liver cancer, leukemia, lymphoma, neuroblastoma, glioma, meningioma, bone cancer, thyroid cancer, breast cancer or prostate cancer. According to an embodiment of this invention, the infectious agent is Hanta virus, HTLV I, HTLV II, HIV, herpes virus, influenza virus, Ebola virus, human papilloma virus, Staphlococcus, Streptococcus, Klebsiella, *E. coli*, anthrax or cryptococcus. According to an embodiment of this invention, the toxin is tetanus, anthrax, botulinum, snake venom or spider venom. In one embodiment of this invention, the tumor is benign. In another embodiment, the enzyme dysfunction is hyperactivity or overproduction of the enzyme. In still another embodiment, the hormone dysfunction is hyperactivity or overproduction of the hormone. In yet another embodiment of this invention, the immune dysfunction is CD3 or CD4 mediated. In still another embodiment of this invention, the autoimmune disease is lupus, thyroidosis, graft versus host disease, transplantation rejection or rheumatoid arthritis. In still another embodiment of the invention, the condition is any abnormality. In still another embodiment, the condition is the normal condition.

Finally, the present invention provides a method of preventing a condition in a subject comprising administering to the subject an amount of the described therapeutic composition, effective to bind the antigen associated with the condition, thereby preventing the condition in the subject. In one embodiment of this invention, the subject previously exhibited the condition. According to one embodiment of this invention, the therapeutic composition is administered to a second subject.

According to an embodiment of this invention, the condition is associated with a cancer, a tumor, a toxin, an infectious agent, an enzyme dysfunction, a hormone dysfunction, an autoimmune disease, an immune dysfunction, a viral antigen, a bacterial antigen, a eukaryotic antigen, rejection of a transplanted tissue, poisoning, or venom intoxication. Additionally the condition may be any other abnormality, including that resulting from infection, cancer, autoimmune dysfunction, cardiovascular disease, or transplantation. In an embodiment of this invention, the condition is septicemia, sepsis, septic shock, viremia, bacteremia or fungemia. In an embodiment of this invention, the cancer is lung cancer, liver cancer, leukemia, lymphoma, neuroblastoma, glioma, meningioma, bone cancer, thyroid cancer, breast cancer or prostate cancer. According to an embodiment of this invention, the infectious agent is Hanta virus, HTLV I, HTLV II, HIV, herpes virus, influenza virus, Ebola virus, human papilloma virus, Staphlococcus, Streptococcus, Klebsiella, *E. coli*, anthrax or cryptococcus. According to an embodiment of this invention, the toxin is tetanus, anthrax, botulinum, snake venom or spider venom. In one embodiment of this invention, the tumor is benign. In another embodiment, the enzyme dysfunction is hyperactivity or overproduction of the enzyme. In still another embodiment, the hormone dysfunction is hyperactivity or overproduction of the hormone. In yet another embodiment of this invention, the immune dysfunction is CD3 or CD4 mediated. In still another embodiment of this invention, the autoimmune disease is lupus, thyroidosis, graft versus host disease, transplantation rejection or rheumatoid arthritis. In still another embodiment of the invention, the condition is any abnormality. In still another embodiment, the condition is the normal condition.

The present invention also provides the production of antibodies for antigens which are not associated with a condition, but more properly constitute a component of the entire repetoire of antibodies in a human immune system.

In addition, the present invention provides identification of novel antigens relevant to a condition in a subject and the use thereof for diagnosis and treatment of the condition in the subject. The invention also provides identification of the repetoire of naturally occurring antibodies in normal subjects and subjects having a pathological condition. In one embodiment, the condition may be venom detoxicification (neutralization). For example, the condition may result from scorpion, spider, rattle snake or poison toad bites or venom exposure. The present invention provides antibodies to act as antidote for such conditions.

The trioma cell of the present invention may also be fused with macrophages, monocytes, T-lymphocytes, and erythroblastoid cells. Hybridoma cells resulting from such fusions may produce growth factors, cytokines, enzymes, hemoglobin As used herein, a human-murine hybridoma (the "immortalizing hybridoma") is an immortal cell line which results from the fusion of a murine myeloma or other murine tumor cell with a human lymphoid cell derived from a normal subject. As described herein below, by careful selection and mutation, an immortalizing hybridoma which provides improved chromosomal stability, has human characteristics, and which does not secrete immunoglobulin may be obtained. The antibody secreting capability of such a resulting trioma may be provided by the third cell fusion which is typically derived either from B cells of an immunized human individual, or with B cells which have been immortalized.

As used herein, a "B6B11" cell is a hybrid cell produced by the fusion of mouse myeloma 653 and human myeloma RPMI 8226.

As used herein, a "B6B11-like" cell is a a hybrid cell produced by the fusion of mouse myeloma 653-related cell and human myeloma RPMI 8226-related cell.

As used herein, a "MFP" cell is a hybrid cell produced by the fusion of a B6B11 cell and a human lymphocyte. B6B11-like cells share function properties and characteristics with B6B11 heteromyeloma cells.

As used herein, a "MFP-like" cell is a hybrid cell produced by the fusion of a B6B11-like cell and a human lymphocyte. MFP-like cells share function properties and characteristics with MFP trioma cells.

As used herein, "non-secreting" or "non-producing" hybridoma refers to a hybridoma which is capable of continuous reproduction and, therefore, is immortal, and which does not produce immunoglobulin.

As used herein, a hybridoma "having human characteristics" refers to a hybridoma which retains detectable human-derived chromosomes such as those producing human HLA antigen which may be expressed on the cell surface.

As used herein, lymphoid cells "immunized against a predefined determinant" refers to lymphoid cells derived from an subject who has been exposed to an antigen having the determinant. For example, a subject can be induced to produce (from its lymphoid B cells) antibodies against the antigenic determinants of various blood types, by exposure, through transfusions or previous pregnancy, or against the antigenic determinants of specific viruses or of bacteria by virus of exposure through past infections or vaccinations.

As used herein, "cell line" refers to various embodiments including but not limited to individual cells, harvested cells and cultures containing cells so long as these are derived from cells of the cell line referred to may not be precisely identical to the ancestral cells or cultures and any cell line referred to include such variants.

As used herein, "trioma" refers to a cell line which contains generic components originating in three originally separate cell linages. These triomas are stable, immortalized cells which result from the fusion of a human-murine hybridoma with a human lymphoid cell.

As used herein, "tetroma" refers to a a cell line which contains generic components originating in four originally separate cell lineages. These tetromas are stable, immortalized antibody producing cells which result from the fusion of a trioma with a human lymphoid cell which is capable of producing antibody.

As used herein, "autologously" refers to a situation where the same subject is both the source of cell immunoglobulin and the target for cells, or immunoglobulin or therapeutic composition.

As used herein, "heterologously" refers to a situation where one subject is the source of cells or immunoglobulin and another subject is the target for the cell, immunoglobulin or therapeutic composition.

In the practice of any of the methods of the invention or preparation of any of the pharmaceutical compositions a "therapeutically effective amount" is an amount which is capable of binding to an antigen associated with the condition. Accordingly, the effective amount will vary with the subject being treated, as well as the condition to be treated. For the purposes of this invention, the methods of administration are to include, but are not limited to, administration cutaneously, subcutaneously, intravenously, parenterally, orally, topically, or by aerosol.

As used herein, the term "suitable pharmaceutically acceptable carrier" encompasses any of the standard pharmaceutically accepted carriers, such as phosphate buffered saline solution, water, emulsions such as an oil/water emulsion or a triglyceride emulsion, various types of wetting agents, tablets, coated tablets and capsules. An example of an acceptable triglyceride emulsion useful in intravenous and intraperitoneal administration of the compounds is the triglyceride emulsion commercially known as Intralipid®.

Typically such carriers contain excipients such as starch, milk, sugar, certain types of clay, gelatin, stearic acid, talc, vegetable fats or oils, gums, glycols, or other known excipients. Such carriers may also include flavor and color additives or other ingredients.

This invention also provides for pharmaceutical compositions capable of binding to an antigen associated with the condition together with suitable diluents, preservatives, solubilizers, emulsifiers, adjuvants and/or carriers. Such compositions are liquids or lyophilized or otherwise dried formulations and include diluents of various buffer content (e.g., Tris-HCl., acetate, phosphate), pH and ionic strength, additives such as albumin or gelatin to prevent absorption to surfaces, detergents (e.g., Tween 20, Tween 80, Pluronic F68, bile acid salts), solubilizing agents (e.g., glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the compound, complexation with metal ions, or incorporation of the compound into or onto particulate preparations of polymeric compounds such as polylactic acid, polglycolic acid, hydrogels, etc, or onto liposomes, micro emulsions, micelles, unilamellar or multi lamellar vesicles, erythrocyte ghosts, or spheroplasts. Such compositions will influence the physical state, solubility, stability, rate of in vivo release, and rate of in vivo clearance of the compound or composition.

Controlled or sustained release compositions include formulation in lipophilic depots (e.g., fatty acids, waxes, oils). Also comprehended by the invention are particulate compositions coated with polymers (e.g., poloxamers or poloxamines) and the compound coupled to antibodies directed against tissue-specific receptors, ligands or antigens or coupled to ligands of tissue-specific receptors. Other embodiments of the compositions of the invention incorporate particulate forms protective coatings, protease inhibitors or permeation enhancers for various routes of administration, including parenteral, pulmonary, nasal and oral.

When administered, compounds are often cleared rapidly from the circulation and may therefore elicit relatively short-lived pharmacological activity. Consequently, frequent injections of relatively large doses of bioactive compounds may by required to sustain therapeutic efficacy. Compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline are known to exhibit substantially longer half-lives in blood following intravenous injection than do the corresponding unmodified compounds (Abuchowski et al., 1981; Newmark et al., 1982; and Katre et al., 1987). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound adducts less frequently or in lower doses than with the unmodified compound.

Attachment of polyethylene glycol (PEG) to compounds is particularly useful because PEG has very low toxicity in mammals (Carpenter et al., 1971). For example, a PEG adduct of adenosine deaminase was approved in the United States for use in humans for the treatment of severe combined immunodeficiency syndrome. A second advantage afforded by the conjugation of PEG is that of effectively reducing the immunogenicity and antigenicity of heterologous compounds. For example, a PEG adduct of a human protein might be useful for the treatment of disease in other mammalian species without the risk of triggering a severe immune response. The carrier includes a microencapsulation device so as to reduce or prevent an host immune response against the compound or against cells which may produce the compound. The compound of the present invention may also be delivered microencapsulated in a membrane, such as a liposome.

Polymers such as PEG may be conveniently attached to one or more reactive amino acid residues in a protein such as the alpha-amino group of the amino terminal amino acid, the epsilon amino groups of lysine side chains, the sulfhydryl groups of cysteine side chains, the carboxyl groups of aspartyl and glutamyl side chains, the alpha-carboxyl group of the carboxy-terminal amino acid, tyrosine side chains, or to activated derivatives of glycosyl chains attached to certain asparagine, serine or threonine residues.

Numerous activated forms of PEG suitable for direct reaction with proteins have been described. Useful PEG reagents for reaction with protein amino groups include active esters of carboxylic acid or carbonate derivatives, particularly those in which the leaving groups are N-hydroxysuccinimide, p-nitrophenol, imidazole or 1-hydroxy-2-nitrobenzene-4-sulfonate. PEG derivatives containing maleimido or haloacetyl groups are useful reagents for the modification of protein free sulfhydryl groups. Likewise, PEG reagents containing amino hydrazine or hydrazide groups are useful for reaction with aldehydes generated by periodate oxidation of carbohydrate groups in proteins.

The present invention describes the production of human monoclonal antibodies directed to tumor-associated antigens, tumor cells, infectious agents, infection-specific antigens, and self antigens using a modified cell fusion partner, trioma cell line and human lymphocytes derived from lymph nodes, spleen, Peyer's patches, or any other lymph tissue or peripheral blood of the human subjects.

Antibodies are selected using cultured cells, purified antigens, primary human cells and tissues and combinatorial libraries relevant to the antibody screening including cells and tissues obtained from autologous donor of lymphoid cells.

This invention is illustrated by examples set forth in the Experimental Details section which follows. This section is provided to aid in an understanding of the invention but is not intended to, and should not be construed to, limit in any way the invention as set forth in the claims which follow thereafter.

EXPERIMENTAL DETAILS

EXAMPLE 1

Construction of Mouse-human Heteromyeloma for the Production of Human Monoclonal antibodies Introduction B6B11 or B6B11-like cells may be produced by the fusion of mouse myeloma cells with human myeloma cells selected for non-secretion of antibody. The specific generation and application of heteromyeloma B6B11, is described herein below. B6B11 was obtained by fusing the mouse HAT-sensitive and G-418 resistant myeloma X63.Ag8.653 with the subclone of human myeloma RPMI 8226 selected for non secretion of lambda light chains. Fusion of human splenocytes and B6B11 cells resulted in a fusion frequency of 30–50 hybrids per $10^7$ cells. This is similar to the frequency of murine hybridoma formation. The hybrids are readily cloned by limiting dilution, produce antibodies for at least 10 month and grow in serum-free media. Two clones were obtained which secreted human IgM reactive against lipopolysaccharide (LPS) of Gram-negative bacteria. These clones were obtained by fusing in vitro immunized human splenocytes with the B6B11 cells. Anti-lipid A murine mAb is known to prevent development of septic shock (Shnyra A A, et al., 1990). Human mAbs have important clinical applications.

Results

Heteromyeloma B6B11. Heteromyeloma, B6B11, was generated by PEG-fusion of mouse myeloma 653 (HAT-sensitive, G-418) with human RPMI 8226, which was selected for non-secretion of lambda chains. Hybrids were selected in the presence of HAT and G-418. Selection for 8-Ag resistance was done by gradually increasing the 8-Ag concentration from 2 ug/ml to 20 ug/ml for 2.5–3 weeks. The HAT-sensitive hybrid population 653×8226 was twice cloned.

Clones were tested for the ability to produce hybrids with human lymphocytes. One clone, designated as B6B11, was selected. B6B11 cells died in medium containing aminopterine, during a period of 5–6 days; no revertants were detected for more than 18 months. In RPMI 1640 supplemented with 10% fetal calf serum (FCS), the line had the doubling time of about 25–30 hours, the maximal density in 75 $cm^2$ flasks was approximately $1.5 \times 10^6$ cells/ml (in a volume of 30 ml). B6B11 culture medium was tested for the presence of human immunoglobulin by enzyme linked immunoassay (ELISA) using rabbit anti-human immunoglobulin. B6B11 exhibited secretion of IgG, IgM or IgA. Staining the cell preparations with MAH-L,H by PAP-technique detected no traces of cytoplasmic light and heavy chain human immunoglobulin.

Figure 1B:
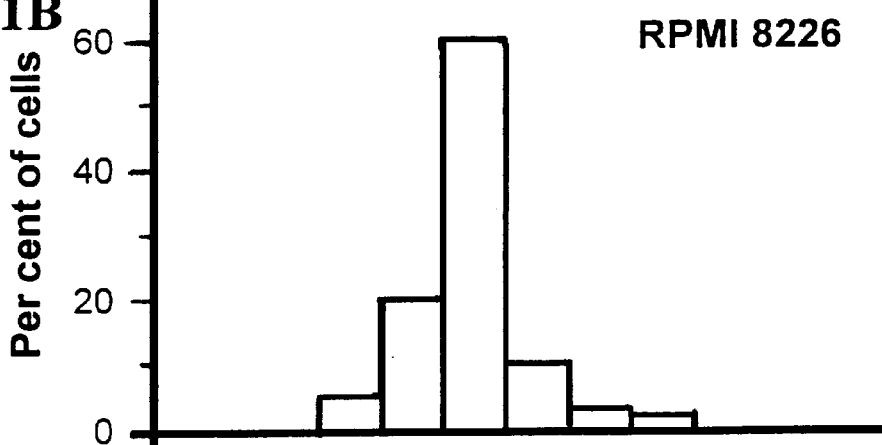
Figure 1C:
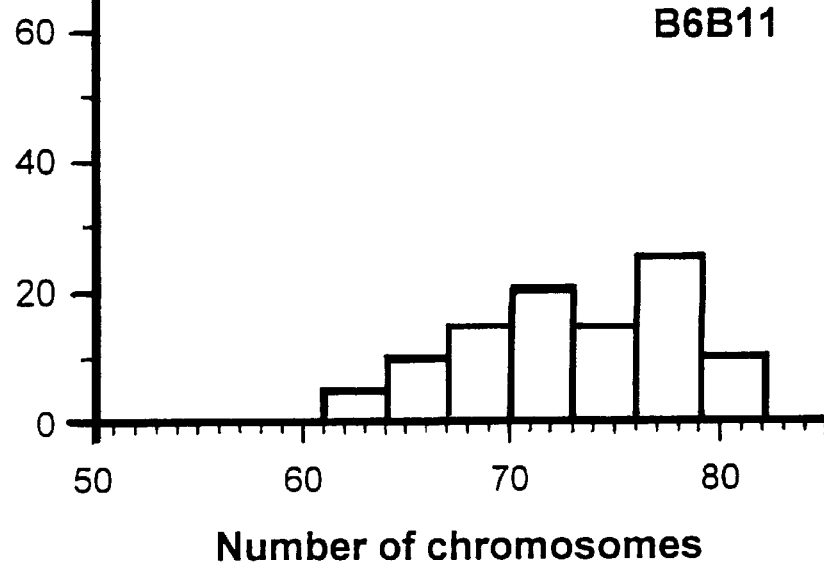

Karyotyping. FIG. 1 illustrates the distribution of parental and B6B11 cells by chromosomal content. Chromosomal analysis of the heteromyeloma cells indicated that chromosomal number varies from 60 to 82.

Figure 2:
FIG. 2 Fragment of G-banded karyotype of B6B11 line. The arrows indicate genetic material presumably of human origin; 3p portion of chromosome 3 and chromosome 19.
Figure 4A:
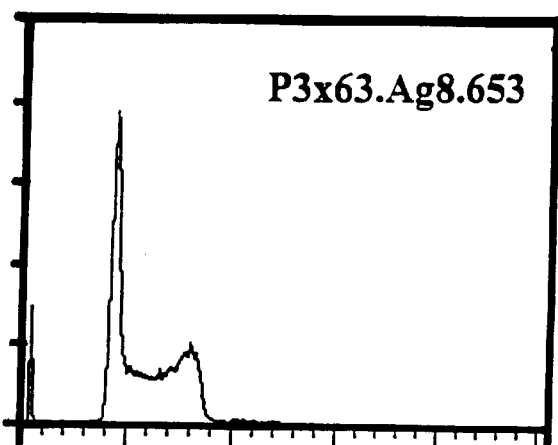
FIGS. 4A–4D DNA histograms of parental cells 653 (FIG. 4A) and 8226 (FIG. 4B), heteromyeloma B6B11 (FIG. 4C) and B6B11-splenocyte hybrid (FIG. 4D). The amount of B6B11 DNA constitutes about 100% of the total amount of 653 DNA plus 8226 DNA. The DNA content of B6B11-SPL hybrid is greater than that of B6B11.
Figure 4B:
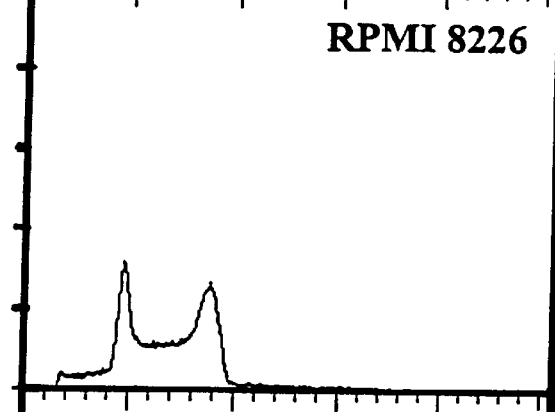
Figure 4C:
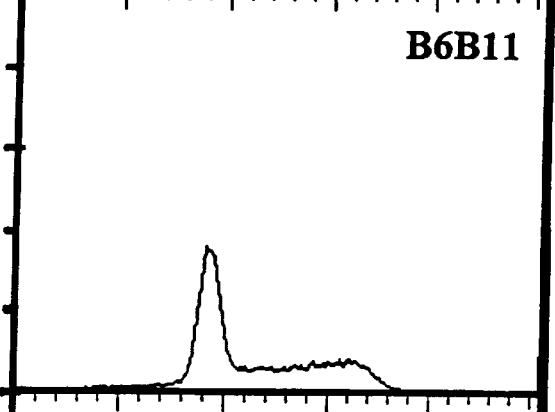
Figure 4D:
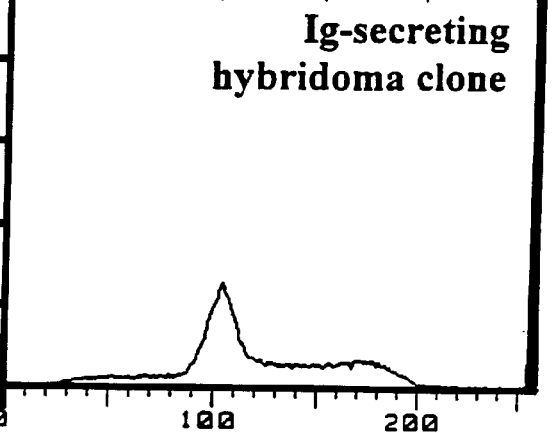

FIG. 2 shows a fragment of the G-banded karyotype of B6B11 cells. Normal mouse chromosomes constitute about 84% of the karyotype. There are several rearranged chromosomes. There are some markers for mouse myeloma chromosomes as well as rearranged heteromyeloma (human-mouse chimeric) chromosomes. One large telocentric chromosome was represented in all B6B11 metaphase plates examined. This suggested that the proximal portion of this chromosome contains mouse and the distal portion contains human genetic material of chromosome 3 (3p21.1-3p ter). Localization of human material was performed as described (33). In some of analyzed B6B11, cells human chromosome 19 and human chromosome 7 was deleted.

Fusion Of B6B11 Cells With Human Lymphocytes. Fusion of B6B11 cells with freshly isolated peripheral blood lymphocytes (PBL) and splenic lymphocytes (SPL) was performed as described herein below in the Experimental Procedures Section. Fusion of peripheral blood lymphocytes (PBL) and pokeweed mitogen (PWM) treated peripheral blood lymphocytes (PBL) resulted in low hybridoma yield (1–5 hybrids per $10^7$ lymphocytes), while fusion with splenic lymphocytes (SPL) and pokeweed mitogen (PWM) treated splenic lymphocytes (SPL) yielded 30–60 hybrids per $10^7$ cells (see Table 1). After the fusion, cells were seeded at a density of $1.5 \times 10^5$ cells per well. Variations in the cell ratios of 1:1 to 1:2 (heteromyeloma:lymphocyte) had no effect on the fusion efficiency for PBL or SPL. However, fusion efficiency was dramatically reduced at B6B11: lymphocyte ratios of 1:4 to 1:8.

TABLE 1

Fusion of human lymphocytes with B6B11 cells.

| | LYMPHOCYTES | | | |
|---|---|---|---|---|
| | PBL | PBL-PWM | SPL | SPL-PWM |
| Number of fusion | 4 | 6 | 10 | 8 |
| Number of wells | 1536 | 2304 | 4800 | 3072 |
| Growth[2], % | 4 | 6, 9 | 55 | 72 |
| Hybrid populations[3] per $10^7$ lymphocytes | 1–3 | 3–5 | 30–50 | 40–60 |
| Wells with Ig secretion[4], % | 95 | 92 | 84 | 82 |

[1]Fresh isolated peripheral blood lymphocytes (PBL) and splenocytes (SPL) were activated with PWM (5 ug/ml) for 7–9 days in complete RPMI 1640 supplemented with 15% FCS.
[2]Wells with hybrids (% of the total well number)
[3]After fusion cells were seeded at a density of $15 \times 10^4$ cells/well
[4]Total Ig production was determined by ELISA with mouse monoclonal antibodies to H- and L-chains of human Ig The effects of splenocyte stimulation with various mitogens on the fusion efficiency are illustrated in FIG. 3. PWM treatment significantly increased the efficiency of SPL hybridization compared with ConA-treatment, PHA-treatment, LPS-treatment or untreated SPL. Fusion efficiency was dependent on the timing of the HAT addition. When HAT was added immediately following fusion, the yield decreased to 10–15 hybrids per $10^7$ lymphocytes (for SPL).

Cloning of hybrids with SPL and PBL (stimulated and non-stimulated) indicated that PBL could not be used for hybridoma formation. Cloning was performed 4–6 weeks after fusion in 50% epithelial conditioned media (ECM) (pre-incubated for 24 hours at 37° C. in 96-well plates) and 50% RPMI 1640 containing 15% FCS. Results were determined at in 2–2.5 weeks. Cloning efficiency (1.5–2 cells per well) was 50–80% for SPL and 10–30% for PBL. ELISA using rabbit anti-human immunoglobulin and MAH-L,H indicated that the total immunoglobulin production was present in 90–95% of growing hybrids with PBL and 80–85% with SPL hybridomas. Based on SPL was selected for PWM stimulation and in vitro immunization.

In order to increase the efficiency of hybridization, splenocytes were treated with 2.5 mM Leu-Ome and fused with B6B11 cells at ratio of 1:1 or 1:2 (B6B11: SPL) (see Table 2). The effect on this treatment was apparent after 18–24 hours of cultivation with PWM; SPL without Leu-Ome treatment exhibited blasts only after three days. The efficiency of hybridization of Leu-Ome-treated SPL was somewhat higher (80%) compared with non-treated SPL (72%). This treatment considerably increased (93%) the number of Ig-secreting hybrids.

TABLE 2

Effect of Leu-Ome treatment of splenocytes on the efficiency of their hybridization with B6B11 cells (data from 3 spleens)

| Lymphocytes | Number of wells | Wells with hybrid populations, (%) | Wells[2] with Ig secretion, (%) |
|---|---|---|---|
| SPL | 1440 | 1034 (72) | 825 (80) |
| SPL-Leu-Ome | 864 | 691 (80) | 642 (93) |

[1]Splenocytes were isolated in LSM. One portion was treated with Leu-Ome (2.5 mM, 40 minutes in serum-free RPMI 1640), the other served as a control. Prior to fusion both portions were cultured for 7 days in complete RPMI 1640 supplemented with 15% FCS in the presence of 5 μg/ml PWM.
[2]Ig production was determined by ELISA with mouse monoclonal antibodies to H- and L-chains of human Ig.

The heteromyeloma cells were fused with Leu-Ome-treated splenocytes immunized with Salmonella Minnesota Re595 (Re595) in the presence of PWM and mouse thymocyte conditioned media (TCM) (Table 3). The hybridoma culture supernatants were tested for anti-bacterial antibodies at different stages of hybrid growth: (1) after transferring responding populations to 24-well plates and (2) after cloning and subsequent clonal expansion. Two independent clones producing anti-bacterial antibodies were selected. ELISA using immobilized lipoplysaccharide (LPS) or immobilized Re595 and LPS in solution determined that the antibodies produced by both clones reacted with LPS.

ELISA using immobilized Re595 monoclonal mouse anti-human isotypes and goat anti-mouse peroxidase conjugate absorbed with human immunoglobulin, determined that the antibody isotype was IgM-kappa. Both clones were adapted to serum free media (SFM) by gradual replacing of the growth medium containing 10% FCS. The maximal density upon culturing in SFM was approximately $1.2 \times 10^6$ cells/ml. SFM-adapted cells were cloned as described above. The efficiency and cloning time were similar to those of the cells cultured in serum-supplemented RPMI 1640 medium.

TABLE 3

Fusion of in vitro immunized splenocytes[1] with B6B11 cells.

| | Number of fusion | | |
|---|---|---|---|
| | 1 | 2 | 3 |
| Number of wells | 288 | 864 | 576 |
| Wells with hybrid populations, (%) | 193 (69) | 734 (85) | 472 (82) |
| Wells with ig secretion, (%) | 173 (90) | 675 (92) | 420 (89) |
| Primary response[2] to Re595, number of wells | 9 (4.5) | — | 17 (3.6) |
| Secondary response[3], number of wells | 2 | — | 16 |
| Number of responding populations after cloning | — | — | 2 |

[1]Splenocytes after treatment with Leu-Ome (2.5 mM, 40 min) were in vitro immunized with S. minnesota Re595 ($10^7$–$10^{10}$ cells/ml) in the presence of PWM (5 ug/ml) and TCM for 7–9 days. Fusions with B6B11 cells were done at ratios 1:1 and 1:2
[2]ELISA of hybridoma culture supernatants from 96-well plates (rabbit anti-human Ig).
[3]ELISA of hybridoma culture supernatants after transferring in 24-well plates (rabbit anti-human Ig).

DNA analysis. FIG. 4 illustrates the distribution of the DNA content by parental lines, B6B11 heteromyeloma and B6B11-splenocyte hybrid. The DNA of heteromyeloma cells consists of 78.7% of the total parental DNA. The DNA content of B6B11-splenocyte hybrid cells is 3% greater than that of B6B11 cells.

Discussion

A partner cell line for production of human monoclonal antibodies was generated by somatic hybridization of mouse X63.Ag8.653 and human RPMI 1640 myeloma cells. Adaptation to medium with 8-Ag, subsequent cloning and selection by hybridization efficiency led to a heterohybrid clone which was designated B6B11. Fusion between heterohybrid lines and lymphocytes gives essentially stable productive hybrids (Raison R L, et al., 1982). The mechanisms underlying this phenomenon are unknown. It is suggested that human chromosomes or their fragments retained in the partner line after the first fusion modify the intracellular environment in such a way that the human lymphocyte chromosomes or fragments after the second fusion are stabilized (Oestberg L, and Pursch E., 1983). The large number of chromosomes, the presence of hybrid marker chromosomes and increased DNA content observed in the experiments described herein, confirmed the hybrid nature of B6B11 cells. The DNA content of B6B11-SPL hybrid cells was also increased. Immunocytochemical testing for intracellular heavy and light chains and ELISA testing for immunoglobulin secretion demonstrated that B6B11 cells produce neither immunoglobulins nor heavy and light chains. Fusion of B6B11 with SPL resulted in more hybrids than fusion with PBL (30–50 per $10^7$ SPL compound to 1–5 per $^710$ PBL). Cloning efficiency with SPL was 50–80% as compared to 10–30% with PBL. Thus SPL were the more preferable partner for fusion. The culture media was conditioned by endothelial cells; which was deemed crucial for viability and clonogeneity of the hybrids. In the case of B6B11-PBL hybrids, immunoglobulin secretion was detected in up to 95% of the hybrids. To increase the yield of immunoglobulin-secreting hybrids after fusion with SPL (up to 93%) Leu-Ome was used. Almost all hybrids secreted antibodies of unknown specificity. The antibody production by B6B11 hybrids was stable for at least 10 months. The hybrids were readily adapted to serum-free media, thereby facilitating a ex-vivo antibody production.

Two antibody-producing clones (with probably similar specificity to LPS of S. minnesota Re595) were obtained after fusion of immunized SPL with B6B11 cells. As demonstrated herein, human-mouse heteromyeloma, B6B11, is useful for producing human monoclonal antibodies to various antigens. Proper in vitro sensitization of lymphocytes is also of critical importance for generating human antibodies.

Experimental Procedures

Cell Culture. 8-Azaguanine (8-Ag) resistant mouse myeloma X63.Ag8.653 (653) cells were transfected with plasmid pBgl-neoR (Dr. A. Ibragimov) as described below. The myeloma cells were maintained in DMEM medium supplemented with 10% fetal calf serum (FCS), 4 mM L-glutamine, 1 mM Sodium pyruvate, non-essential amino acids and vitamins (Flow Laboratories). Prior to fusion the cells were passaged 3 times in the presence of 20 µg/ml 8-Ag (Sigma) and 500 µg/ml G-418 (Gibco).

Human myeloma cell line RPMI 8226 (8226) was cultured in RPMI 1640 medium with above-mentioned supplements (regular RPMI 1640). The hybrid heteromyeloma B6B11 was cultured either in regular RPMI 1640 with 10% FCS or in serum-free media which represented 1:1 mixture of Iscove's modification of Dulbecco medium (IMDM) and HAM F-12 (Flow Laboratories) supplemented with bovine serum albumin fraction #5, 2 mg/ml, (BSA) (Sigma), bovine insulin, 5 µg/ml (Serva), human transferrin, 5 µg/ml (Sigma), progesterone, 6 ng/ml (Gibco), hydrocortisone, 60 ng/ml (Gibco). Hybridomas were adapted to this serum free medium (SFM) by gradual replacement of the growth medium containing 10% FCS. All cells were cultured in a humidified atmosphere of 5.5% $CO_2$/94.5% air at 37° C.

Human peripheral blood lymphocytes (PBL) were isolated using lymphocytes separation medium (LSM) (Flow Laboratories) as per manufacturer instructions. Spleens collected at autopsy not later than 2 hours after death (males aged 50–60 years old) were homogenized and splenocytes (SPL) were isolated in LSM.

Production of Geneticin (G-418) Resistant 653 Myeloma Cells. Cells were washed in sterile phosphate buffered saline (PBS) without $Ca^{++}$ or $Mg^{++}$. pBgl-neoR Plasmid DNA linearized by BamH1 (constructed by P. Chumakov, Institute of Molecular Biology of the Academy of Sciences of the USSR, Moscow, USSR) was added to the cell suspension. Prior to adding the DNA to the cell suspension, the DNA was twice phenol extracted using phenol-ether at 4° C., 96% ethanol precipitated and dried under sterile conditions.

Transfection was performed by electroporation at 4° C. using a unit constructed by L. Chernomordik (Institute of Electrical Chemistry of the Academy of Sciences of the USSR, Moscow, USSR). Approximately $4 \times 10^6$ 653 myeloma cells and 3.5 µg of plasmid DNA were combined in an 80 µl electroporation chamber. The final concentration of DNA was 44 µg/ml). An electrical current impulse of 1.7 Kv/cm was pulsed through the chamber for 100 µsec. After resting for 10 minutes the cells were transferred to 0.5 ml complete media in 16 $mm^2$ wells at $5 \times 1^30$ and $2 \times ^410$ cells/well. After 36 hours, 0.5 ml of media containing 1 mg/ml of Geneticin (G-418) was added to a final concentration of 0.5 mg/ml. Subsequently, 50% of the media volume was changed every 2 days for 12 days.

Production of heteromyeloma. G-418-resistant 653 cells were mixed with 8226 cells at a 1:1 ratio and pelleted. 50% (v/v) polyethylenglycol (PEG) 3350 (Sigma) was added (200–300 µl per $4–5 \times 10^7$ cells) for 1 min with constant stirring. Several portions of serum-free RPMI 1640 (RPMI-S⁻) were added for 5 minutes (first 10 ml), 1 minute (10 ml), and 1 minute (30 ml). Cells were pelletted resuspended in regular RPMI 1640 with 20% FCS, hypoxanthine ($1 \times 10^4$ M), aminopterine ($4 \times 10^7$ M), thymidine ($1,6 \times 10^5$ M) (HAT, Flow Laboratories) and 500 µg/ml G-418 and seeded in 96-well plates (Linbro) at a density of $10^5$ cells per well. At two weeks the medium (½ volume) was replaced with medium containing hypoxanthine ($2 \times 10^4$ M), thymidine ($3.2 \times 10^5$ M) (HT, Flow laboratories) and G-418 (500 µg/ml). The procedure was repeated after two weeks.

Production of human monoclonal antibodies. Fusion of B6B11 cells with human lymphocytes was accomplished by the above-described method with following modifications. Lymphocytes were mixed with B6B11 at a 1:1 or a 1:2 ratio, pelleted, washed with RPMI 1640-S- and incubated with PEG (600 µl per $10^5$ cells) for 3 minutes with constant stirring. The portions of added RPMI-S- were as follows: 10 ml/10 minutes, 10 ml/10 5 minutes, 10 ml/1 minute. Cells were pelleted, re-suspended in regular RPMI supplemented with 15% FCS and seeded in 96-well plates ($1.5 \times 10^5$ cells per well). HAT-medium was added after 24 hours. The growth medium (½ volume) was replaced with fresh HAT in 7–9 days. HAT-medium was replaced with HT-medium at 15–18 days.

Cloning. Parent heteromyeloma and hybridoma cells were cloned by the limiting dilution method in medium conditioned by human umbilical or aortic endothelial cells (Antonov A S, et al., 1986) (gift from Dr. A. Antonov) (ECM). 100 μl/well was incubated in 96-well plates at 37° C. overnight. Cells were planted at approximately 1 to 2 cells per well. The culture medium was tested for antibodies at 2.5–3 weeks.

Immunization in vitro. Freshly isolated lymphocytes were resuspended in RPMI-S- containing 2.5 mM L-leucine methyl ester (Leu-OMe) (Borrebaeck, CAK, et al., 1987) to a final concentration of $10^7$ cells per ml. After 40 minutes of incubation at room temperature, cells were washed 3 times with RPMI-S- and resuspended in regular RPMI 1640 supplemented with 15% FCS. Medium conditioned by mouse thymocytes (TCM) was used as a source of lymphokines (Reading C L., 1982). Pokeweed mitogen (PWM) (Flow laboratories) to a final concentration 5 μg/ml, TCM (25%) and antigen in different concentrations were added to the cell suspension. The cell suspension (4–6×$10^6$ cell/ml) was transferred to flasks (30 ml/75 cm² flask). Fusion was performed after 7–9 days of cultivation. Concanavalin A (ConA) (Flow 5–10 μg/ml), Phytohemagglutinin (PHA) (Flow, 5–10 μg/ml) and lipopolysaccharide (LPS) (SIGMA, 10–15 μg/ml) were used instead of PWM. S. minnesota Re595 (gift of Dr. O. Luderitz, Max Plank Institute fur Immunologie, Feiburg, Germany) was used as an antigen. The bacteria were grown in medium containing 16 g/l tryptic soy broth (TSB), Difco), 16 g/l brain-heart infusion (BHI) (Difco) and 4 g/l yeast extract (YE) (DIFCO) for 18 hours at 37° C. with constant stirring and then heat inactivated. The antigen concentration varied from $10^{7-10^{10}}$ cells/ml.

Determination of antibodies and non-specific Ig production. Enzyme linked immunoassay (ELISA) was used to test hybridoma supernatants for the presence of antibodies against Salmonella minnesota Re595 and LPS.

Screening for mAbs reactive against bacteria. 96-well plates were covered with glutaraldehyde (1%, 100 μl per well) for 2 hours at room temperature. The plates were washed with distilled water 3 times. Bacteria were resuspended in 50 mM ammonium carbonate buffer (pH 9.6) and transferred to plates (5×$10^7$ cells in 100 μl per well), centrifuged at 780×g for 30 minutes and washed with distilled water 4 times. The supernatants tested (100 μl) were supplemented with 0.1% Tween 20 (Fluka), put into bacteria-containing wells and incubated for 1 hour at room temperature. The media was then removed and the wells were washed with distilled water. Affinity purified rabbit anti-human immunoglobulin conjugated to alkaline phosphatase (RAH-AP), diluted in tris-buffered solution (TBS, 50 mM, pH 7.4), containing 0.1% Tween 20 was added to 1 μg in 100 μl per well. After 1 hour of incubation at room temperature and 6 washes with distilled water 100 μl of 4-nitrophenyl-phosphate (1 mg/ml, Sigma) in diethanolamine buffer (10% diethanolamine, 0.5 mM Mgcl2, pH 9.8) was added. After 1 hour, the results were read using a Multiscan (Flow Laboratories) at 405 nm. The negative control was culture medium RPMI 1640 supplemented with 15% FCS.

Screening for mAbs reactive against lipopolysaccharide. LPS was purified from Salmonella Minnesota Re595 as described (Galanos G, et al., 1969). The LPS preparation was sonicated and transferred to the plates at 2.5 μg per well in 5mM ammonium carbonate buffer (pH 9.6). After overnight incubation at room temperature, the above described procedures for determining mAb reactive against bacteria were performed.

Screening for non-specific production of mAbs. Non-specific production of immunoglobulin and separate chains was assessed after the addition of 100 μl of rabbit anti-human immunoglobulin (10 μg/ml in phosphate buffer, PBS, pH 7.2) or 100 μl/well (10 ng/ml in PBS) of mouse monoclonal antibodies to light and heavy chains of human immunoglobulin (MAH-L, H) (Rokhlin O V, 1989) (gift of O. Rochlin, C R C, Moscow). Subsequent procedures were performed as described above.

Determination of the isotype of secreted antibodies. The isotype of human antibodies was determined by ELISA using murine anti-human light and heavy chains (MAH-L, H) and goat anti-mouse immunoglobulin (25 ug/ml) conjugated to peroxidase and absorbed with human immunoglobulin.

Determination of cytoplasmic light or heavy chains production. Production of cytoplasmic light and/or heavy chains in hybridomas, B6B11 and the parental cell lines was estimated immunocytochemically using the peroxidase-anti-peroxidase system (PAP). Cell smears were air-dried, fixed for 45 seconds with 10% formaldehyde (v/v) and 45% acetone (v/v) in phosphate buffered saline (PBS, 10 mM $NaH_2PO_4$, pH 6.6) and incubated with MAH-L,H (200 μl, 5–10 mg/ml). Then 1 ml rabbit anti-mouse immunoglobulin (38 mg/ml in PBS) was added. All incubations were 30 minutes. Washings were performed using PBS for 10 minutes.

Chromosomal analysis. Preparations of metaphase chromosomes were obtained by the following technique. Colchicine was added to cells during exponential growth (1.5–2 hours to parental lines and B6B11 cells). Cells were then trypsinized and stained for G-banding as described (Seabright S., 1971) (10–15 plates from each line). To count chromosome number, at least 50 metaphase figures were analyzed for each cell line.

DNA analysis by flow cytometry. To estimate the DNA content the cells (1×$10^6$) were fixed with 1 ml 70% ethanol, washed, incubated for 2–3 hours with 0.3 mg/ml Ribonuclease A (Serva) in Hank's solution (pH 7.4) and stained for 2 hours with propidium iodide (0.05 mg/ml, Sigma) in Hank's solution. The DNA content was measured in a FACS-II cytofluorometer (Becton Dickinson). Fluorescence was excited by an argon ion laser at 488 nm (164–05 Model, Spectra-Physics) at a power of 400 mW and registered behind a 600 nm long pass interference filter (Ditric Optica).

Parental lines. The myeloma line 653 was maintained in DMEM supplemented with 10 FCS, 20 ng/ml 8-Azaguanine and 500 μg/ml G-418. The myeloma line 8226 producing lambda chains of human Ig was cultured in RPMI-C containing 10% FCS. In order to create a heteromyeloma, a non-producing clone of 8226 line was selected by cloning in ECM (2 cells per well). Lambda chain production was estimated at 2–2.5 weeks using MAH-L, H. The frequency of non-secreting clones was 1×$10^3$.

EXAMPLE 2

Trioma MFP-2, a Fusion Partner for Generating Human Monoclonal Antibodies

Introduction

A precursor hybridoma cell line was obtained by hybridization of the commercially available human myeloma cell line RPMI 8226 and mouse myeloma X63.Ag8.653 resistant to both 8-Azaguanine (8-Ag) and Geneticin 418 (G-418). One of the resulting clones, B6B11, was selected in the presence of G-418. B6B11 was grown in the presence of increased concentrations of 8-Ag and is resistant to both G-418 and 8-Ag (See Example 1).

Although B6B11 can be used to make human hybridomas by fusing with human lymph node-derived lymphocytes or spleen-derived lymphocytes, B6B11 was not capable of fusing with human peripheral blood lymphocytes (PBL) or resulted in a very low yield of hybrids (see example 1).

In order to overcome this problem, B6B11 was fused with human lymph node lymphocytes and several hybrids were obtained. The resulting cells were analyzed for human immunoglobulin production or production of separate immunoglobulin chains. Those clones, which did not synthesize immunoglobulin or immunoglobulin chains were selected for further evaluation in terms of fusion capability and antibody secretion potential. These hybrids were determined to be quite stable. These fusion products were designated "modified fusion partner" (MFP) cells. These MFP cells as the product of the fusion of the B6B11 hybridoma and lymphocytes are referred to herein as "trioma" cells because they are, in essence, the product of a three fused cells. One of the clones, MFP-2, exhibited a very high efficiency for fusing with peripheral blood lymphocytes as well as for fusing with human lymphocytes of any varied origin (i.e. lymph nodes, spleen, Peyer's patches etc). MFP-2 was selected on the basis of its superior characteristics and stability as a fusion partner and was used in the experiments described herein below.

The products of fusions between the MFP trioma cells and lymphocytes are referred to herein as "tetroma" cells becase they are, in essence, the product of four fused cells.

Results

Immunoglobulin Production. In order to demonstrate that human hybrioma (trioma) fusion partner cell line, MFP-2, is capable of fusing with human lymphocytes and producing high yields of hybrids with stable immunoglobulin production, experiments were performed using human lymphocytes from different sources.

Figure 5A:
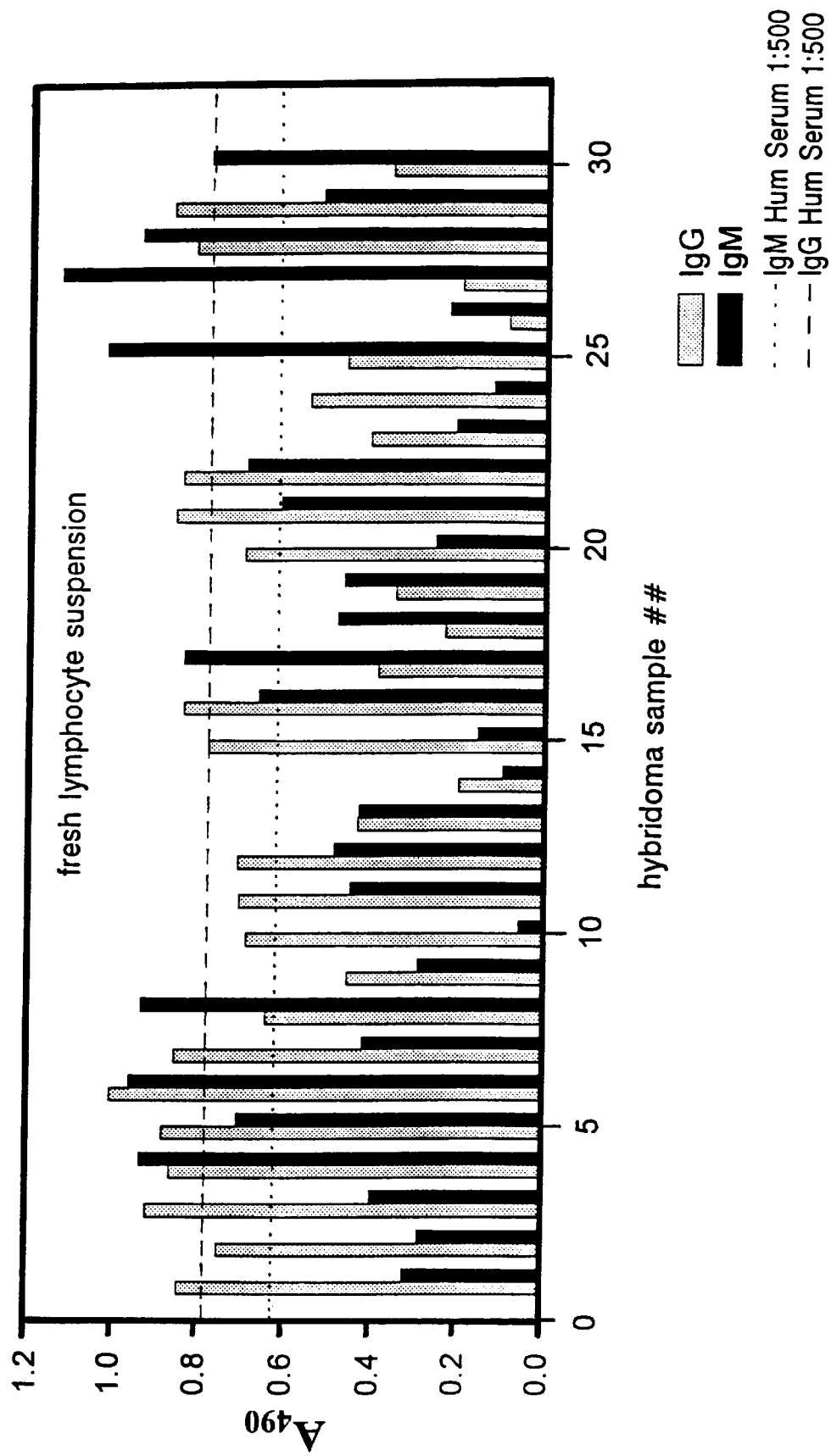

The heteromyeloma cell line, B6B11 (precursor to MFP-2), can be fused with high efficiency with lymph node and spleen lymphocytes. (See, Example 1). Up to 90% of the resulting hybrids produced IgG or IgM. However, B6B11 was incapable of fusing to lymphocytes derived from peripheral blood (PBLs). The trioma cell line, MFP-2, (resulting from a fusion between B6B11 and human lymph node lymphocytes) overcame this problem and exhibited high fusion efficiency with PBL, yielding a high rate of immunoglobulin production by the resulting tetroma hybrids. The capability of MFP-2 to fuse with PBL was tested in two ways: (1) by fusion with freshly isolated lymphocytes in suspension, and (2) by fusion with thawed lymphocytes which had been stored frozen for various periods of time. (See Experimental Procedures). The results of these experiments are shown in FIG. 5.

The fusion efficiency was $10^5$ (1 hybrid per $10^5$ lymphmphocytes). Thirty primary hybridoma (tetroma) populations were obtained and analyzed for capacity to secrete immunoglobulin. (A primary hybridoma population is likely to be a mixture of two or more individual clones). Twenty-seven populations (90%) produced IgM at a level 5-fold greater than background. Twenty-four populations (80%) secreted IgE at a level 5-fold greater than background. The fusion of MFP-2 with lymphocyte suspensions which had been frozen and thawed also resulted in immunoglobulin-producing hybrids. Nineteen percent and 11% of these hybridoma populations produced human IgM and IgG respectively. The efficiency of fusion, itself, was not effected by the freeze-thaw procedure. These results demonstrate that both freshly isolated as well as frozen PBLs can be used to generate human hybridomas capable of producing antibody.

Identification of tumor-associated antigens and production of specific antibodies using the MFP-2 fusion partner: Human monoclonal antibodies against thyroglobulin. In this experiment, human anti-thyroglobulin antibodies were generated by MFP-2 fusion using lymph nodes from patients diagnosed with thyroid adenocarcinoma. A periclavicular lymph node was excised during lymphadenectomy surgery from a female thyroid cancer patient and lymphocytes were isolated and fused with MFP-2, generating tetroma cells.

Figure 6:
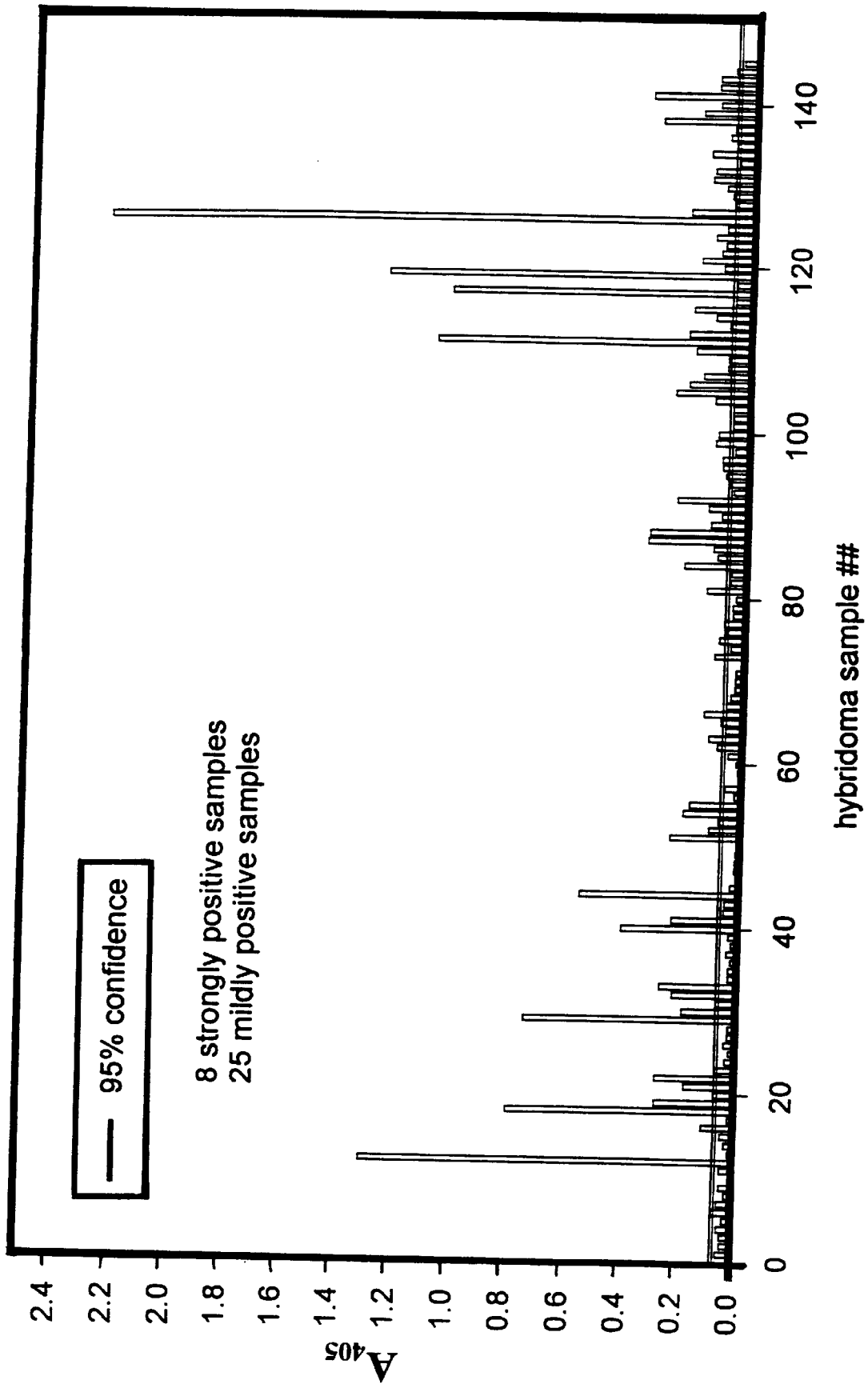
FIG. 6 Anti-thyroglobulin antibody production by thyroid cancer lymph node lymphocytes fused to fusion partner MFP-2 cells. The Y-axis indicates optical density at $A_{405}$ ($OD_{405}$) for different hybridoma samples (tetromas) generated from fusion with the MFP-2 trioma line (X-axis). Thirty-three tetromas produced antibody which reacted positively against thyroglobulin; eight were particularly strongly reactive.

The resulting hybridomas (tetromas) were tested for production of human antibodies reactive against thyroglobulin using an enzyme linked immunoassay (ELISA) procedure. Purified human thyroglobulin was used to coat a microtitre plate. Results are shown in FIG. 6. Thirty-three of 144 tetromas exhibited a response against the thyroglobulin antigen. Eight of these were particularly strong. (See FIG. 6). Thus, lymph node-derived tetromas from this thyroid cancer patient were producing anti-thyroglobulin antibodies. This was an unexpected and surprising result because the patient had no known history of autoimmune (i.e. anti-thyroid antibodies) disease. This suggests that the antibodies produced in this patient to thyroglobulin were induced by the presence of cancerous thyroid adenocarcinoma cells. Cancerous thyroid adenocarcinoma cells are known to secrete thyroglobulin. This experiment demonstrates that tumor cells can induce a humoral immune response to tumor-associated antigens and that the antibody-producing cells can be identified and immortalized through the techniques described herein using the MFP-2 fusion partner in order to produce human anti-tumor monoclonal antibodies.

Production of human monoclonal antibodies against breast cancer associated antigens. In another experiment, human monoclonal antibodies were produced against cancer associated antigens using lymph node and peripheral blood lymphocytes from breast cancer patients. Axillary lymph nodes were excised from breast cancer patients who underwent mastectomy or lumpectomy. Lymphocytes isolated from these lymph nodes were fused to MFP-2 and the resulting tetromas were screened against breast cancer cell lines MCF7, SK-BR-3, ZR-75-1. Nearly all the tetromas were producing IgG or IgM (approximately 85% and 10% respectively). Surprisingly, nearly 15% of the tetromas assayed against breast cancer cell lines produced antibodies specifically directed against cancer cells. The tetroma supernatants were tested in two ways: (1) on a live cells in the CELISA (cellular ELISA) assay and (2) by Western blotting using cell lysates. The molecular weight range of the specific antigens recognized by human monoclonal antibodies was 25 to 160 kDA. In order to delineate the nature of the antigenic target, immunoprecipitation followed by microsequencing is performed. In addition, random peptide combinatorial libraries are used to identify the molecular targets of the cancer-specific antibodies.

In one patient with Stage IV breast cancer, lymph nodes were not available so PBLs were fused to MFP-2 and 156 tetromas were obtained. The tetromas were analyzed for immunoglobulin production as well as for cancer-specific antibody production. IgM was produced by 28 tetromas; 87 tetromas produced IgG. Four of the IgM antibodies and seven of the IgG antibodies were identified as reactive against cellular antigens; three IgM anti-bodies and four IgG antibodies were specific for breast cancer cells. The rest of the tetromas exhibited immunoreactivity against other cell types including human prostate cancer cell lines, human diploid fibroblasts and human skin fibroblasts. These latter antibodies were probably directed to common antigens (common for normal and cancerous cells).

The PBLs were isolated from the blood of a patient who received 77 cycles of chemotherapy which would reasonably be expected to have a depressing effect on the patient's immune system. None-the-less, this patient still produced anti-cancer antibodies suitable for fusing with MFP-2.

Human tetromas generated from fusing MFP-2 and prostate cancer lymphocytes are tested for the presence of PSA-specific antibodies as well as antibodies directed to prostate cancer cell lines LNCaP, DU-145, and PC-3.

Production of human antibodies against infectious disease-associated antigens. Infectious diseases are commonly accompanied by a well-developed humoral and cellular immune response. Patients with certain infections often contain large numbers of specific antibody producing cells. One important application of the antibody immunotherapy described by the present invention, is the production of human monoclonal antibodies to proinflammatory cytokines which are involved in septic shock. Among these targets are cytokines such as tumor necrosis factor $\alpha$ (TNF-$\alpha$) and interleukin-1a (IL-1a). Additional targets include other cytokines and lymphokines, infectious agents and their toxins, including tetanus toxin, anthrax toxin, botulinum toxin, and lipid A. The peripheral blood of patients infected with bacteria, fungi, protozoa or viruses typically contains circulating antibody-producing cells which can be isolated and used as a source for fusion with MFP-2. For example, PBLs from patients with septic shock, Hanta virus infection, HIV, HTLV-I, HTLV-II, influenza, hepatitis, or herpes virus can be fused with MFP-2 and the resulting tetroma cells can be screened against the respective antigens. In AIDS, in particular, patient lymphocytes can be immortalized using the techniques described herein in order to generate bulk quantities of anti-HIV antibodies for use in passive immunotherapy in an autologous or heterologous manner.

Production of human antibodies against autoimmune disease. A general consideration for the use of human monoclonal antibodies in autoimmune disease is to block autoantibodies, or to block CD4$^+$ T cells which are involved in autoimmune cellular cytotoxicity. In one approach, human monoclonal antibodies against CD4$^+$ cells are generated following fusion with the MFP-2 trioma cell. Resulting tetroma cells which produce anti-CD4 antibodies are used to reduce or deplete CD4$^+$ T cells, thereby relieving autoimmune cellular attack. In another approach MFP-2 is used to generate tetroma cells capable of producing anti-idiotypic antibodies directed to specific autoantibodies. For example, autoimmune thyroiditis is an autoimmune dysfunction in which there is a high titer of anti-thyroglobulin antibodies in a patient's plasma. PBL-derived lymphocytes are isolated from such patients for fusion with MFP-2. The resultant tetroma cells are screened for those capable of producing antibodies with a substantial anti-idiotypic immune response directed against the autoantibodies reactive with thyroglobulin. These anti-idiotypic antibodies are then used to modulate the autoimmune disease by reducing or depleting the anti-thyroglobulin antibodies. Such an approach may be used autologously or heterologously. In an autologous approach, the anti-idiotypic antibody-producing cells are identified in peripheral blood of the patient to be treated, then isolated and fused with MFP-2 and following selection for specific anti-anti-thyroglobulin antibodies, passively administered to the original patient. In a heterologous approach, the anti-anti-thyroglobulin antibodies are administered to a different patient.

Other Applications: Preventing rejection of transplanted organs, blood clotting. Among other applications of human monoclonal antibodies, is prevention of organ transplant rejection by blocking T cells through the OKT-3 (anti-CD3) marker. Antibodies to adhesion molecules (anti-integrin antibodies) also prevent migration of immune cells, which is important, for example in rheumatoid arthritis. Blood clotting may be modulated, for example, in acute cardiac ischemia following coronary angioplasty, using human monoclonal antibodies against GPIIb/IIIa of platelet. Intravenous infusion of immunoglobulins helps to neutralize the Fc-receptor mediated cell aggregation of platelet or other blood cells (e.g. thromobytopenic purpura).

In addition, this approach may be used to detoxify or neutralize toxin or venom exposure. Such exposures include, but are not limited to snake, spider or poison toad bites or yellow jacket or scorpion stings. The horse anti-serum currently used to neutralize rattle snake venom causes serum sickness disease in 30% of cases.

There is a shortage of natural human immunoglobulin required for these kinds of treatments. The human monoclonal antibody production system described herein facilitates production, in vitro, of unlimited quantities of human immunoglobulins which can be selected to fit particular need. For example, in the case of immunoglobulin which blocks Fc receptors, instead of treating the patient with the pooled preparation of immunoglobulins where only a small fraction of molecules possess the required qualities, the immunoglobulin preparation of the molecules with the required properties can be produced using the fusion partner described herein.

Discussion

There has long been a need for human monoclonal antibodies for diagnosis, treatment, and monitoring of cancer. Attempts to employ xenoantibodies in clinical trials have not produced promising results. Non-human antibodies from mice, for example, cause development of a human anti-mouse immune response, sensitization to foreign protein which may eventually result in anaphylactic reaction, and lack of biological effect since the effector properties of the xenoantibodies may mismatch the components of the human immune system. Human monoclonal antibodies have numerous advantages. One is that human monoclonal antibodies can identify those tumor-associated antigens (TAA) which are immunogenic only in humans, while xenoantibodies in most cases recognize those antigens and antigenic epitopes which express immunodominance in a host and are often the tissue specific epitopes. Another advantage is the well-developed interaction of human monoclonal antibodies with the effector components (such as complement) of the host immune system. In addition, allergic and/or anaphylactic reaction to the injectible human monoclonal antibodies is less of a concern since human monoclonal antibodies are syngenic in human subjects. Alternative attempts have been made to develop antibodies such as chimeric antibodies (partially human, partially murine), where the Fc part of the murine immunoglobulin was substituted with the human IgG-Fc. Humanized antibodies, are human immunoglobulins grafted with the CDR regions of the specific murine antibodies. Single chain (Fc) human antibodies have been developed in phage using phage display libraries. A downside of these approaches is that the resulting antibodies are not natural; they have not emerged as part of a natural immune response to cancer or infectious agent.

Use of the hybridoma techniques described herein and the availability of the MFP-2 trioma fusion partner cell line described herein, facilitates identification, immortalization, and ex-vivo expansion of antibody-producing cells which emerge in vivo as a result of natural humoral immune responses to an antigen. Since such cells are a part of the natural immune system response, the antibodies produced by these cells dovetail with the other components of the immune system and are able to provide an effective and specific biological response.

A number of breast cancer specific antigens have been described which are potential targets for the immunotherapy of cancer, including HER2/neu, Mucin 1 and Mucin 2, p53, c-myc, blood antigens T, Tn and sialyl-Tn, tuncated form of EGF, Lewis-Y antigen and others. The presence of circulating antibodies to these antigens have also been described in cancer patients. (G. Moller, 1995). Lymph nodes are important sites of such antibody-producing cells. By isolating lymph node (or peripheral blood) lymphocytes and immortalizing them by fusing them with human hybridoma fusion partner MFP-2, hybrids (tetromas), which produce antibodies directed against cancer-associated antigens may be obtained. As described above, specific monoclonal antibody producing cells are identified and may be produced in unrestricted fashion, ex-vivo (using bioreactors, SCID mice, etc). The antibodies may be used therapeutically as passive immunotherapy either autologously in the same subject or heterologously in a different subject. Even another cancer may be treated, provided there is an overlapping tumor antigen.

Syngenic or allogenic use of human monoclonal antibody can be highly effective since such an antibody can be infused many times without the risk or threat of developing an anti-xenogenic immune response. The infused antibodies, depending on their effector functions, can initialize complement dependent cytolysis of the target tumor cells, or antibody-dependent cellular cytotoxicity antibody dependent cellular cytotoxicity (ADCC) (by NK or CTL cells), or provide direct cytotoxic effect through apoptosis.

Summary

A unique fusion partner cell line, MFP, was obtained which can be used to generate specific human monoclonal antibodies. These monoclonal antibodies may be in vivo based on a natural immune response to infectious agents, cancer cells or an autoimmune dysfunction, or can be in vitro based by immunization of human lymphoid cells in vitro.

The methods described herein for generating specific monoclonal antibodies may be used to provide adoptive humoral immunotherapy either as an autologous procedure or as a heterologous procedure. Lymphocytes isolated from a patient with a cancer or infectious disease are immortalized by fusion with MFP-2. The resulting tetromas, producing antibodies directed to the respective antigens, are selected in vitro. Following selection, these antibody-producing cells are expanded and antibodies may be produced using a bioreactor or immune-deficient mice (e.g., nude mice or SCID mice). Such antibodies may then be used for the treatment of the original donor as an autologous adoptive immunotherapy procedure or for the treatment of a different subject as a heterologous, adoptive immunology procedure.

The developed antibodies may also be applied both to invasive diagnostics (imaging, immunoscintigraphy) or therapy (drug targeting, radioimmunotherapy, complement-dependent cytolysis, ADCC, apoptotic cytolysis etc.)

This approach also provides a method for identification of novel tumor markers or novel infectious agent antigens. The immune system responds to cancer cells or infectious agents by producing antibodies directed to different components of the foreign formation and can recognize different neo-epitopes. Fusing tumor reactive or infectious agent antigen reactive immunoglobulin with MFP-2 can be used to identify novel tumor markers or infectious antigens. Such antibodies are important in treatment against specific cancers or infectious agents, and in the generation of specific imaging and diagnostic techniques. Previous attempts to generate human anti-tumor or anti-infectious antibodies required forced or artificial immunization of a subject with purified or isolated antigen. In the present invention, the antigen may be unknown; the starting material for developing antibodies is the pool of immunocompetent lymphocytes which evolved as a part of natural immune response to the foreign antigens presented in their natural form and in natural environment in vivo. In an autologous application, selection can be conducted using an autologous tissue of interest (e.g. tumor biopsies) which will increase the chances to select the right antibody. Also, autologous blood plasma and white blood cells can be used to select for cytotoxic antibodies from the same donor.

Thus, the MFP fusion partner (1) allows fusion with peripheral blood lymphocytes yielding high levels of hybrids; (2) allows consideration of an adoptive humoral immunotherapy on an individual basis (selection of the antibodies against tumor cells or infectious agents derived from the same donor the lymphocytes were obtained from and the autologous treatment of the patient); (3) fusion with the donor's lymphocytes undergoing immunization in vitro; (4) allows use of frozen lymphocytes or lymphocytes derived from plasmapheresis as a source of antibody-producing cells.

Experimental Procedures

Hybridoma fusion partner MFP-2 was developed as a trioma cell line by fusing non-producing heteromyeloma B6B11 with human lymphocytes isolated from the paraclavicular lymph node.

Isolation of lymphocytes. Paraclavicular lymph nodes from a patient diagnosed with metastatic thyroid cancer were excised during the surgery and placed into sterile conservation media RPMI1640 supplemented with L-glutamine (4 mM), non essential amino acids (100×stock), vitamins (100×stock), sodium pyruvate (1 mM) and Gentamicin (2×concentration). Lymph node tissue was transferred to a 100 mm tissue culture TC dish in the same media and gently disrupted with forceps and scissors. The disrupted tissue was passed through a metal sieve (50 mesh) using a glass pestle. The suspension was transferred into 15 ml sterile conical tubes containing lymphocyte separation media (Histopaque 1.077 Sigma) as an underlying layer at a ratio of 2:1 (lymphocytes suspension: Histopaque). Following centrifugation at 400×g for 20 minutes, an opaque ring formed at the border between layers. Red blood cells (RBC) were present as a pellet at the bottom of the tube. If RBC are not present in the starting lymphocyte suspension (which is a quite normal situation for lymph nodes) the separation step can be skipped. The opaque ring containing lymphocytes was carefully collected using a Pasteur pipette and was diluted 10-fold diluted with regular serum-free RPMI 1640. Cells were spun at 300×g for 10 minutes and washed twice with media.

The final lymphocyte suspension was diluted with media and cells were counted using 0.05% Trypan Blue. Cell viability after isolation was usually 95%. Total yield was approximately $4 \times 10^7$ cells.

Preparation of B6B11. Heteromyeloma B6B11 was grown in RPMI 1640 with 10% cosmic calf serum (Hyclone), standard set of supplements (L-Glu, 4 mM non-essential amino acids, vitamins, Sodium Pyruvate) without antibiotics. Before fusion, cells were cultured in the presence of 8-Ag (20 μg/ml) to avoid reversion of HAT-sensitive cells to wildtype. Cells were grown to a density of 10% in logarithmic growth phase.

Cell fusion. Both B6B11 cells and lymph node lymphocytes were washed 3 times by centrifugation at 300×g for 5 minutes in order to remove any residential protein in the media. Cells were mixed at a ratio of 5:1 (lymphocyte:myeloma) and spun at 300×g for 10 minutes. The supernatant was carefully and completely removed the pellet was "puffed" gently and 100 μl of PEG/DMSO solution warmed to room temperature was added to the cell mixture which was gently tapped for 3 minutes. Then 15 ml of Hank's Balanced Salt Solution (HBSS) and PBS (1:1)(from a 10×stock, Cellgro) were added as follows: 10 ml slowly in 10 minutes, then 5 ml over 5 minutes, then 10 ml of complete media (media for cell culturing) over 5 minutes and finally 5 ml over 1 minute. The total volume was 30 ml. Then 600 μl of HT solution (of 10×stock) and 1 drop (about 20–30 μl) of DMSO were added to the tube. The cell suspension was mixed in a tube, transferred to Petri dish (100×15) and incubated in a 37° C. $CO_2$ incubator overnight. The cells were then harvested, pelleted at 300×g for 10 minutes and resuspended in complete media supplemented with HAT-solution and HT-solution (both from 50×stock) and then plated into 96-well plates in a 200 μl volume at about 250,000 cells per well. Twice a week, 50% of the media was replaced with fresh media. Cells were cultured in the presence of HAT and HT for 14–20 days before screening for antibody production.

ELISA screening for nonspecific immunoglobulin. ELISA plates were coated with polyclonal goat-anti-human IgG (Fc-specific) (Sigma), goat-anti-human IgM (μ-specific) (Sigma) or goat-anti-human Ig(G+M+A) H-chains (Sigma) in 100 μl of plating buffer (0.1 M Sodium Carbonate, pH 9.0) at 100 ng per well. The plates were sealed with Parafilm or sealing covers and incubated overnight at 4° C. The antigen was washed out with distilled water twice. Residual drops of water were removed and 200 μl of blocking solution (0.4% dry non-fat milk in PBS) was added to the wells. Complete cell culture media served as a negative control. Human serum (1:2000) was used as a positive control. Plates were incubated for 2 hours at room temperature or overnight at 4° C. The plates were washed 4 times with distilled water and secondary antibodies (same as capture antibodies but conjugated to HRP) diluted in 0.4% milk/PBS at 1:2000 were added to the wells. After 1 hour incubation at room temperature the wells were washed 4 times with $H_2O$ and peroxidase substrate (ortophenylendiamine in phosphate-citrate buffer with peroxide) was added to the plates. The color reaction was stopped by adding 20 μl of 10% sulfuric acid. Colorimetric reading was performed on a Multiscan reader at $A_{492}$. Samples which exhibited at least a 3-fold increase over background were considered to be immunoglobulin-producing cells.

Assay for the intracellular (non-secreted) presence of immunoglobulins or their individual chains. Cells which did not secrete immunoglobulin in the supernatant culture media were tested for the presence of intracellular immunoglobulin-immunoreactive material. ELISA plates were coated with goat-anti-human kappa chain (Sigma), goat-anti-human lambda chain (Sigma) and goat-anti-human IgH (G,M,A) as described above. Cells were grown in 75 $cm^2$ flasks to the density $10^6$ cells per ml, harvested and washed 3 times with HBSS. Cells were resuspended in PBS and disrupted by sonication (8×15 seconds at 25 MHz on ice). The suspension was spun for 15 minutes at 10,000×g and the supernatant was used for immunoglobulin testing. An equivalent of $2\times10^6$ cells was used. As a negative control mouse fibroblasts 3T3 were used at the same protein amount equivalent. The rest of the protocol was the same as described above for the hybridoma supernatant testing. Clones which showed the signal equal to the control cells or lower were chosen as potential candidates for fusion with human peripheral blood lymphocytes. These trioma clones were designated as modified fusion partner series (MFP-S) and numbered sequentially (MFP-1, MFP-2, MFP-3, etc.) Six non-producing, non-secreting triomas were selected for further analysis.

Selection for 8-Ag resistant MFP mutants. To use MFP trioma cells as fusion partners, the MFP cells were placed in complete media containing an increasing amounts of 8-Ag. Resistance to 8-Ag is determined by the impaired enzyme HGPRT or its absence. Selection was therefore focused on cells which survived in the presence of 8-Ag. After 5 to 10 passages at the lower concentrations of 8-Ag (5 μg/ml) the survivors were cultured in media with a higher concentration (10 μg/ml). This was repeated until a concentration of 20 μg/ml was reached. After 5–6 passages in the presence of 8-Ag (20 μg/ml) cells were tested for their viability in HAT-media. None of the cells grown on 8-Ag survived after 3 days of culture in the presence of HAT.

Fusion efficiency. The MFP clones were tested for ability to fuse with lymph node lymphocytes and PBL. MFP-2 yielded approximately 2–3 hybrids per $10^5$ lymph node lymphocytes and 0.7–1.5 hybrids per $10^5$ of PBL. The immunoglobulin secretion rate for the hybrids developed using MFP-2 ranged between 0.5 to 15 ug/ml with no decrease over 7 months.

REFERENCES

Kohler G, and Milstein C., Nature 1975; 256:495
Levy, R., and Miller R A. Federation Proceedings 1983; 42:2650.
Posner M R, et al., Hybridoma 1983; 2:369.
Kozbor D, and Roder J., J.Immunology 1981; 127:1275.
Casual O, Science 1986; 234:476.
Glassy M C, Proc.Natl.Acad.Sci (USA) 1983; 80:6327.
Ollson L, et al., J.Immunol.Methods 1983; 61:17
Nilsson K. and Ponten J., Int.J.Cancer 1975; 15:321
Goldman-Leikin R E, J.Lab.Clin.Med. 1989: 113:335.
Brodin T, J.Immunol.Meth. 1983; 60:1.
Teng N N H, Proc.Natl.Acad.Sci. (USA) 1983; 80:7308.
Weiss M C, and Green H. Proc.Natl.Acad.Sci. (USA) 1967; 58:1104.
Oestberg L, and Pursch E., Hybridoma 1983; 2:361
Kozbor D, et. al., J.Immunology 1984; 133:3001
Shnyra A A, et al., In: Friedman H, Klein T W, Nakano M, Nowotny A, and Eds. Advances in Exp. Medicine & Biology Endotoxin New York: Plenum, 1990; 256:681.
Antonov A S, et al., Atherosclerosis 1986; 59:1.
Borrebaeck C A K, et al., Biochem.Biophys.Res.Commun. 1987; 148:941.
Reading C L., J.Immunol. Meth. 1982; 53:261.
Galanos G, et al., Eur.J.Biochem 1969; 9:245.
Rokhlin O V, 8th Int. Congress of Immunology, Berlin. Abstracts 1989; 6.
Seabright S., Lancet 1971; 2:971.
Yunis J J., Cancer Genetics and Cytogenetics 1980; 2:221.
Raison R L, et al., J.Exp.Medicine 1982; 156:1380.

Moller, G, 1995. (editor) Immunological Reviews Vol 145: Tumor Immunology.

What is claimed is:

1. A trioma cell which does not produce any antibody obtained by fusing a heteromyeloma cell which does not produce any antibody with a human lymphoid cell, wherein the heteromyeloma cell is designated B6B11 (ATCC Designation number HB-12481).

2. The trioma cell of claim 1, wherein the human lymphoid cell is a myeloma cell.

3. The trioma cell of claim 1, wherein the human lymphoid cell is a splenocyte or a lymph node cell.

4. The trioma cell of claim 1, wherein the trioma cell is designated MFP-2 (ATCC Designation number HB-12482).

5. A tetroma cell capable of producing a monoclonal antibody having specific binding affinity for an antigen obtained by fusing the trioma cell of claim 1 with a human lymphoid cell capable of producing antibody having specific binding affinity for the antigen.

6. The tetroma cell of claim 5, wherein the human lymphoid cell is selected from the group consisting of a peripheral blood lymphocyte, a splenocyte, a lymph node cell, a B cell, a T cell, a tonsil gland lymphocyte, a monocyte, a macrophage, an erythroblastoid cell and a Peyer's patch cell.

7. The tetroma cell of claim 5, wherein the antigen is selected from the group consisting of a tumor-associated antigen, a cell specific antigen, a tissue-specific antigen, an enzyme, a nucleic acid, an immunoglobulin, a toxin, a viral antigen, a bacterial antigen and a eukaryotic antigen.

8. A trioma cell generated by a method comprising:

(a) fusing a heteromyeloma cell which does not produce antibody with a human lymphoid cell thereby forming a trioma cell;

(b) incubating the trioma cell formed in step (a) under conditions permissive to the production of antibody by the trioma cell; and (c) selecting a trioma cell that does not produce antibody, wherein the heteromyeloma cell of step (a) is designated B6B11 (ATCC Designation number HB-12481).

9. A tetroma cell generated by a method comprising:

(a) fusing the trioma cell of claim 1 with a human lymphoid cell thereby forming a tetroma cell;

(b) incubating the tetroma cell formed in step (a) under conditions permissive to the production of antibody by the tetroma cell; and (c) selecting a tetroma cell capable of producing a monoclonal antibody.

* * * * *